(12) United States Patent
Bruder et al.

(10) Patent No.: US 9,254,316 B2
(45) Date of Patent: Feb. 9, 2016

(54) ADENOVIRAL VECTOR-BASED MALARIA VACCINES

(71) Applicants: Joseph T. Bruder, Ijamsville, MD (US); C. Richter King, New York, NY (US); Thomas Richie, Glenelg, MD (US); Keith Limbach, Gaithersburg, MD (US); Denise Louise Doolan, Camp Hill (AU)

(72) Inventors: Joseph T. Bruder, Ijamsville, MD (US); C. Richter King, New York, NY (US); Thomas Richie, Glenelg, MD (US); Keith Limbach, Gaithersburg, MD (US); Denise Louise Doolan, Camp Hill (AU)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/890,422

(22) Filed: May 9, 2013

(65) Prior Publication Data
US 2014/0335128 A1 Nov. 13, 2014

(51) Int. Cl.
*A61K 39/00* (2006.01)
*A61K 39/015* (2006.01)
*C07H 21/04* (2006.01)
*C12N 7/00* (2006.01)

(52) U.S. Cl.
CPC ............. *A61K 39/015* (2013.01); *C12N 7/00* (2013.01); *A61K 2039/53* (2013.01); *C12N 2710/10043* (2013.01)

(58) Field of Classification Search
CPC .............................. A61K 39/015; C07H 21/04
USPC .............. 424/9.1, 9.2, 184.1, 185.1, 234.1, 424/265.1, 268.1, 269.1, 272.1; 536/23.1, 536/23.7
See application file for complete search history.

(56) References Cited

U.S. PATENT DOCUMENTS

2005/0031592 A1* 2/2005 Doolan et al. ............... 424/93.2

FOREIGN PATENT DOCUMENTS

WO WO2004/055187 * 1/2004 ............ C12N 15/30

* cited by examiner

*Primary Examiner* — Rodney P Swartz
(74) *Attorney, Agent, or Firm* — Ning Yang; Albert M. Churilla; Diane Tso

(57) ABSTRACT

The invention provides a method of inducing an immune response against malaria in a mammal. The method comprises intramuscularly administering to a mammal a composition comprising a pharmaceutically acceptable carrier and either or both of (a) a first adenoviral vector comprising a nucleic acid sequence encoding a *P. falciparum* circumsporozoite protein (CSP) operably linked to a human CMV promoter, and/or (b) a second adenoviral vector comprising a nucleic acid sequence encoding a *P. falciparum* apical membrane antigen 1 (AMA-1) antigen operably linked to a human CMV promoter.

24 Claims, No Drawings

SEQUENCE LISTING

```
<160> NUMBER OF SEQ ID NOS: 17

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Cys Arg Gly Asp Cys
1               5

<210> SEQ ID NO 2
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: "Xaa" may be any amino acid
<220> FEATURE:
<221> NAME/KEY: MISC_FEATURE
<222> LOCATION: (8)..(8)
<223> OTHER INFORMATION: "Xaa" may be any amino acid

<400> SEQUENCE: 2

Cys Xaa Cys Arg Gly Asp Cys Xaa Cys
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Cys Asp Cys Arg Gly Asp Cys Phe Cys
1               5

<210> SEQ ID NO 4
<211> LENGTH: 1803
<212> TYPE: DNA
<213> ORGANISM: Artificial
<220> FEATURE:
```

<223> OTHER INFORMATION: Synthetic

<400> SEQUENCE: 4

| | | | | | |
|---|---|---|---|---|---|
| atgggccaga | actactggga | gcacccctac | cagaactccg | acgtgtaccg | ccccatcaac | 60 |
| gagcaccgcg | agcaccccaa | ggagtacgag | taccccctgc | accaggagca | cacctaccag | 120 |
| caggaggact | ccggcgagga | cgagaacacc | ctgcagcacg | cctacccccat | cgaccacgag | 180 |
| ggcgccgagc | ccgcccccca | ggagcagaac | ctgttctcct | ccatcgagat | cgtggagcgc | 240 |
| tccaactaca | tgggcaaccc | ctggaccgag | tacatggcca | agtacgacat | cgaggaggtg | 300 |
| cacggctccg | gcatccgcgt | ggacctgggc | gaggacgccg | aggtggccgg | cacccagtac | 360 |
| cgcctgccct | ccggcaagtg | ccccgtgttc | ggcaagggca | tcatcatcga | gaactccaac | 420 |
| accaccttcc | tgaccccccgt | ggccaccggc | aaccagtacc | tgaaggacgg | cggcttcgcc | 480 |
| ttccccccca | ctgagcccct | gatgtccccc | atgaccctgg | acgagatgcg | ccacttctac | 540 |
| aaggacaaca | gtacgtgaa | gaacctggac | gagctgaccc | tgtgctcccg | ccacgccggc | 600 |
| aacatgatcc | ccgacaacga | caagaactcc | aactacaagt | accccgccgt | gtacgacgac | 660 |
| aaggacaaga | agtgccacat | cctgtacatc | gccgcccagg | agaacaacgg | ccccccgctac | 720 |
| tgcaacaagg | acgagtccaa | gcgcaactcc | atgttctgct | ccgcccccgc | caaggacatc | 780 |
| tccttccaga | actacaccta | cctgtccaag | aacgtggtgg | acaactggga | gaaggtgtgc | 840 |
| ccccgcaaga | acctgcagaa | cgccaagttc | ggcctgtggg | tggacggcaa | ctgcgaggac | 900 |
| atcccccacg | tgaacgagtt | ccccgccatc | gacctgttcg | agtgcaacaa | gctggtgttc | 960 |
| gagctgtccg | cctccgacca | gcccaagcag | tacgagcagc | acctgaccga | ctacgagaag | 1020 |
| atcaaggagg | gcttcaagaa | caagaacgcc | tccatgatca | agtccgcctt | cctgcccacc | 1080 |
| ggcgccttca | aggccgaccg | ctacaagtcc | cacggcaagg | gctacaactg | ggcaactac | 1140 |
| aacaccgaga | cccagaagtg | cgagatcttc | aacgtgaagc | ccacctgcct | gatcaacaac | 1200 |
| tcctcctaca | tcgccaccac | cgccctgtcc | caccccatcg | aggtggagaa | caacttcccc | 1260 |
| tgctcccctgt | acaaggacga | gatcatgaag | gagatcgagc | gcgagtccaa | gcgcatcaag | 1320 |
| ctgaacgaca | cgacgacga | gggcaacaag | aagatcatcg | cccccccgcat | cttcatctcc | 1380 |
| gacgacaagg | actccctgaa | gtgcccctgc | gaccccgaga | tggtgtccaa | ctccacctgc | 1440 |
| cgcttcttcg | tgtgcaagtg | cgtggagcgc | gcgccgagg | tgacctccaa | caacgaggtg | 1500 |
| gtggtgaagg | aggagtacaa | ggacgagtac | gccgacatcc | ccgagcacaa | gcccacctac | 1560 |
| gacaagatga | agatcatcat | cgcctcctcc | gccgccgtgg | ccgtgctggc | caccatcctg | 1620 |
| atggtgtacc | tgtacaagcg | caagggcaac | gccgagaagt | acgacaagat | ggacgagccc | 1680 |
| caggactacg | gcaagtccaa | ctcccgcaac | gacgagatgc | tggacccccga | ggcctccttc | 1740 |
| tggggcgagg | agaagcgcgc | ctcccacacc | accccccgtgc | tgatggagaa | gccctactac | 1800 |
| taa | | | | | | 1803 |

<210> SEQ ID NO 5
<211> LENGTH: 600
<212> TYPE: PRT
<213> ORGANISM: Artificial
<220> FEATURE:
<223> OTHER INFORMATION: Synthetic

<400> SEQUENCE: 5

Met Gly Gln Asn Tyr Trp Glu His Pro Tyr Gln Asn Ser Asp Val Tyr
1               5                   10                  15

-continued

```
Arg Pro Ile Asn Glu His Arg Glu His Pro Lys Glu Tyr Glu Tyr Pro
             20                  25                  30

Leu His Gln Glu His Thr Tyr Gln Gln Glu Asp Ser Gly Glu Asp Glu
         35                  40                  45

Asn Thr Leu Gln His Ala Tyr Pro Ile Asp His Glu Gly Ala Glu Pro
     50                  55                  60

Ala Pro Gln Glu Gln Asn Leu Phe Ser Ser Ile Glu Ile Val Glu Arg
 65                  70                  75                  80

Ser Asn Tyr Met Gly Asn Pro Trp Thr Glu Tyr Met Ala Lys Tyr Asp
                 85                  90                  95

Ile Glu Glu Val His Gly Ser Gly Ile Arg Val Asp Leu Gly Glu Asp
            100                 105                 110

Ala Glu Val Ala Gly Thr Gln Tyr Arg Leu Pro Ser Gly Lys Cys Pro
        115                 120                 125

Val Phe Gly Lys Gly Ile Ile Ile Glu Asn Ser Asn Thr Thr Phe Leu
    130                 135                 140

Thr Pro Val Ala Thr Gly Asn Gln Tyr Leu Lys Asp Gly Gly Phe Ala
145                 150                 155                 160

Phe Pro Pro Thr Glu Pro Leu Met Ser Pro Met Thr Leu Asp Glu Met
                165                 170                 175

Arg His Phe Tyr Lys Asp Asn Lys Tyr Val Lys Asn Leu Asp Glu Leu
            180                 185                 190

Thr Leu Cys Ser Arg His Ala Gly Asn Met Ile Pro Asp Asn Asp Lys
        195                 200                 205

Asn Ser Asn Tyr Lys Tyr Pro Ala Val Tyr Asp Lys Asp Lys Lys
    210                 215                 220

Cys His Ile Leu Tyr Ile Ala Ala Gln Glu Asn Asn Gly Pro Arg Tyr
225                 230                 235                 240

Cys Asn Lys Asp Glu Ser Lys Arg Asn Ser Met Phe Cys Phe Arg Pro
                245                 250                 255

Ala Lys Asp Ile Ser Phe Gln Asn Tyr Thr Tyr Leu Ser Lys Asn Val
            260                 265                 270

Val Asp Asn Trp Glu Lys Val Cys Pro Arg Lys Asn Leu Gln Asn Ala
        275                 280                 285

Lys Phe Gly Leu Trp Val Asp Gly Asn Cys Glu Asp Ile Pro His Val
    290                 295                 300

Asn Glu Phe Pro Ala Ile Asp Leu Phe Glu Cys Asn Lys Leu Val Phe
305                 310                 315                 320

Glu Leu Ser Ala Ser Asp Gln Pro Lys Gln Tyr Glu Gln His Leu Thr
                325                 330                 335

Asp Tyr Glu Lys Ile Lys Glu Gly Phe Lys Asn Lys Asn Ala Ser Met
            340                 345                 350

Ile Lys Ser Ala Phe Leu Pro Thr Gly Ala Phe Lys Ala Asp Arg Tyr
        355                 360                 365

Lys Ser His Gly Lys Gly Tyr Asn Trp Gly Asn Tyr Asn Thr Glu Thr
    370                 375                 380

Gln Lys Cys Glu Ile Phe Asn Val Lys Pro Thr Cys Leu Ile Asn Asn
385                 390                 395                 400

Ser Ser Tyr Ile Ala Thr Thr Ala Leu Ser His Pro Ile Glu Val Glu
                405                 410                 415

Asn Asn Phe Pro Cys Ser Leu Tyr Lys Asp Glu Ile Met Lys Glu Ile
            420                 425                 430

Glu Arg Glu Ser Lys Arg Ile Lys Leu Asn Asp Asn Asp Asp Glu Gly
```

```
            435                 440                 445
Asn Lys Lys Ile Ile Ala Pro Arg Ile Phe Ile Ser Asp Asp Lys Asp
    450                 455                 460

Ser Leu Lys Cys Pro Cys Asp Pro Glu Met Val Ser Asn Ser Thr Cys
465                 470                 475                 480

Arg Phe Phe Val Cys Lys Cys Val Glu Arg Ala Glu Val Thr Ser
                485                 490                 495

Asn Asn Glu Val Val Lys Glu Tyr Lys Asp Glu Tyr Ala Asp
            500                 505                 510

Ile Pro Glu His Lys Pro Thr Tyr Asp Lys Met Lys Ile Ile Ile Ala
        515                 520                 525

Ser Ser Ala Ala Val Ala Val Leu Ala Thr Ile Leu Met Val Tyr Leu
    530                 535                 540

Tyr Lys Arg Lys Gly Asn Ala Glu Lys Tyr Asp Lys Met Asp Glu Pro
545                 550                 555                 560

Gln Asp Tyr Gly Lys Ser Asn Ser Arg Asn Asp Glu Met Leu Asp Pro
                565                 570                 575

Glu Ala Ser Phe Trp Gly Glu Glu Lys Arg Ala Ser His Thr Thr Pro
            580                 585                 590

Val Leu Met Glu Lys Pro Tyr Tyr
        595                 600

<210> SEQ ID NO 6
<211> LENGTH: 1869
<212> TYPE: DNA
<213> ORGANISM: Artificial
<220> FEATURE:
<223> OTHER INFORMATION: Synthetic

<400> SEQUENCE: 6
atgcgcaagc tgtactgcgt gctgctgctg tccgccttcg agttcaccta catgatcaac    60
ttcggccgcg ccagaactac tgggagcac ccctaccaga actccgacgt gtaccgcccc    120
atcaacgagc accgcgagca ccccaaggag tacgagtacc ccctgcacca ggagcacacc    180
taccagcagg aggactccgg cgaggacgag aacaccctgc agcacgccta ccccatcgac    240
cacgagggcg ccgagcccgc ccccaaggag cagaacctgt ctcctccat cgagatcgtg    300 gagcgctcca actacatggg caaccctcg accgagtaca tggccaagta cgacatcgag    360
gaggtgcacg gctccggcat ccgcgtggac ctgggcgagg acgccgaggt ggccggcacc    420
cagtaccgcc tgccctccgg caagtgcccc gtgttcggca agggcatcat catcgagaac    480
tccaagacaa cgttcctgac cccgtggcc accggcaacc agtacctgaa ggacggcggc    540
ttcgccttcc ccccaccga gcccctgatg tccccatga ccctggacga gatgcgccac    600
ttctacaagg acaacaagta cgtgaagaac ctggacgagc tgaccctgtg ctcccgccac    660
gccggcaaca tgatcccga caacgacaag aactccaact acaagtaccc cgccgtgtac    720
gacgacaagg acaagaagtg ccacatcctg tacatcgccg cccaggagaa caacggcccc    780
cgctactgca caaggacga gtccaagcgc aactccatgt ctgcttccg ccccgccaag    840 gacatctcct tccagcagta tacgtacctg tccaagaacg tggtggacaa ctgggagaag    900
gtgtgccccc gcaagaacct gcagaacgcc aagttcggcc tgtgggtgga cggcaactgc    960
gaggacatcc ccacgtgaa cgagttcccc gccatcgacc tgttcgagtg caacaagctg   1020
gtgttcgagc tgtccgcctc cgaccagccc aagcagtacg agcagcacct gaccgactac   1080
gagaagatca aggagggctt caagaacaag caggcctcca tgatcaagtc cgccttcctg   1140
```

```
cccaccggcg ccttcaaggc cgaccgctac aagtcccacg gcaagggcta caactgggc    1200
aactacaaca ccgagaccca gaagtgcgag atcttcaacg tgaagcccac ctgcctgatc    1260
cagcagagct cctacatcgc caccaccgcc ctgtcccacc ccatcgaggt ggagaacaac    1320
ttcccctgct ccctgtacaa ggacgagatc atgaaggaga tcgagcgcga gtccaagcgc    1380
atcaagctga cgacaacga cgacgagggc aacaagaaga tcatcgcccc ccgcatcttc    1440
atctccgacg acaaggactc cctgaagtgc ccctgcgacc ccgagatggt gtcccagtcc    1500
acgtgccgct tcttcgtgtg caagtgcgtg gagcgccgcg ccgaggtgac ctccaacaac    1560
gaggtggtgg tgaaggagga gtacaaggac gagtacgccg acatcccga gcacaagccc     1620
acctacgaca agatgaagat catcatcgcc tcctccgccg ccgtggccgt gctggccacc    1680
atcctgatgg tgtacctgta caagcgcaag ggcaacgccg agaagtacga caagatggac    1740
gagccccagg actacggcaa gtccaactcc cgcaacgacg agatgctgga ccccgaggcc    1800
tccttctggg gcgaggagaa gcgcgcctcc cacaccaccc ccgtgctgat ggagaagccc    1860
tactactaa                                                            1869
```

<210> SEQ ID NO 7
<211> LENGTH: 622
<212> TYPE: PRT
<213> ORGANISM: Artificial
<220> FEATURE:
<223> OTHER INFORMATION: Synthetic

<400> SEQUENCE: 7

```
Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
        35                  40                  45

Lys Glu Tyr Glu Tyr Pro Leu His Gln Glu His Thr Tyr Gln Gln Glu
    50                  55                  60

Asp Ser Gly Glu Asp Asn Thr Leu Gln His Ala Tyr Pro Ile Asp
65                  70                  75                  80

His Glu Gly Ala Glu Pro Ala Pro Gln Glu Gln Asn Leu Phe Ser Ser
                85                  90                  95

Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
        115                 120                 125

Val Asp Leu Gly Glu Asp Ala Glu Val Ala Gly Thr Gln Tyr Arg Leu
    130                 135                 140

Pro Ser Gly Lys Cys Pro Val Phe Gly Lys Gly Ile Ile Ile Glu Asn
145                 150                 155                 160

Ser Lys Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
    210                 215                 220
```

```
Ile Pro Asp Asn Asp Lys Asn Ser Asn Tyr Lys Tyr Pro Ala Val Tyr
225                 230                 235                 240

Asp Asp Lys Asp Lys Cys His Ile Leu Tyr Ile Ala Ala Gln Glu
            245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Gln Tyr Thr
        275                 280                 285

Tyr Leu Ser Lys Asn Val Val Asp Asn Trp Glu Lys Val Cys Pro Arg
        290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
                340                 345                 350

Tyr Glu Gln His Leu Thr Asp Tyr Glu Lys Ile Lys Glu Gly Phe Lys
            355                 360                 365

Asn Lys Gln Ala Ser Met Ile Lys Ser Ala Phe Leu Pro Thr Gly Ala
370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415

Thr Cys Leu Ile Gln Gln Ser Ser Tyr Ile Ala Thr Thr Ala Leu Ser
                420                 425                 430

His Pro Ile Glu Val Glu Asn Asn Phe Pro Cys Ser Leu Tyr Lys Asp
            435                 440                 445

Glu Ile Met Lys Glu Ile Glu Arg Glu Ser Lys Arg Ile Lys Leu Asn
450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
            485                 490                 495

Val Ser Gln Ser Thr Cys Arg Phe Phe Val Cys Lys Cys Val Glu Arg
            500                 505                 510

Arg Ala Glu Val Thr Ser Asn Glu Val Val Lys Glu Glu Tyr
            515                 520                 525

Lys Asp Glu Tyr Ala Asp Ile Pro Glu His Lys Pro Thr Tyr Asp Lys
530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Tyr Gly Lys Ser Asn Ser Arg Asn
            580                 585                 590

Asp Glu Met Leu Asp Pro Glu Ala Ser Phe Trp Gly Glu Glu Lys Arg
            595                 600                 605

Ala Ser His Thr Thr Pro Val Leu Met Glu Lys Pro Tyr Tyr
            610                 615                 620

<210> SEQ ID NO 8
<211> LENGTH: 1866
<212> TYPE: DNA
```

<213> ORGANISM: Artificial
<220> FEATURE:
<223> OTHER INFORMATION: Synthetic

<400> SEQUENCE: 8

```
atgcgcaagc tgtactgcgt gctgctgctg tccgccttcg agttcaccta catgatcaac    60
ttcggccgcg gccagaacta ctgggagcac ccctaccaga actccgacgt gtaccgcccc   120
atcaacgagc accgcgagca ccccaaggag tacgagtacc ccctgcacca ggagcacacc   180
taccagcagg aggactccgg cgaggacgag aacaccctgc agcacgccta ccccatcgac   240
cacgagggcg ccgagcccgc cccccaggag cagaacctgt tctcctccat cgagatcgtg   300
gagcgctcca actacatggg caaccctgg accgagtaca tggccaagta cgacatcgag   360
gaggtgcacg gctccggcat ccgcgtggac ctgggcgagg acgccgaggt ggccggcacc   420
cagtaccgcc tgccctccgg caagtgcccc gtgttcggca agggcatcat catcgagaac   480
tccaagacaa cgttcctgac ccccgtggcc accggcaacc agtacctgaa ggacggcggc   540
ttcgccttcc cccccaccga gccctgatg tcccccatga ccctggacga gatgcgccac   600
ttctacaagg acaacaagta cgtgaagaac ctggacgagc tgaccctgtg ctcccgccac   660
gccggcaaca tgatccccga caacgacaag aactccaact acaagtaccc cgccgtgtac   720
gacgacaagg acaagaagtg ccacatcctg tacatcgccg cccaggagaa caacggcccc   780
cgctactgca acaaggacga gtccaagcgc aactccatgt tctgcttccg ccccgccaag   840
gacatctcct tccagaacct ggtctacctg tccaagaacg tggtggacaa ctgggagaag   900
gtgtgccccc gcaagaacct gcagaacgcc aagttcggcc tgtgggtgga cggcaactgc   960
gaggacatcc cccacgtgaa cgagttcccc gccatcgacc tgttcgagtg caacaagctg  1020
gtgttcgagc tgtccgcctc cgaccagccc aagcagtacg agcagcacct gaccgactac  1080
gagaagatca aggagggctt caagaacaag aaccgggaga tgatcaagtc cgccttcctg  1140
cccaccggcg ccttcaaggc cgaccgctac aagtcccacg gcaagggcta caactggggc  1200
aactacaaca ccgagaccca gaagtgcgag atcttcaacg tgaagcccac ctgcctgatc  1260
aacgacaaga actacatcgc caccaccgcc ctgtcccacc catcgaggt ggagaacaac  1320
ttccccctgct ccctgtacaa ggacgagatc atgaaggaga tcgagcgcga gtccaagcgc  1380
atcaagctga cgacaacga cgacgagggc aacaagaaga tcatcgcccc ccgcatcttc  1440
atctccgacg acaaggactc cctgaagtgc cctgcgacc ccgagatggt gtcccagtcc  1500
acgtgccgct tcttcgtgtg caagtgcgtg gagcgccgcg ccgaggtgac ctccaacaac  1560
gaggtggtgg tgaaggagga gtacaaggac gagtacgccg acatccccga gcacaagccc  1620
acctacgaca gatgaagat catcatcgcc tcctccgccg ccgtggccgt gctggccacc  1680
atcctgatgg tgtacctgta caagcgcaag ggcaacgccg agaagtacga caagatggac  1740
gagccccagg actacggcaa gtccaactcc cgcaacgacg agatgctgga ccccgaggcc  1800
tccttctggg gcgaggagaa gcgcgcctcc cacaccaccc ccgtgctgat ggagaagccc  1860
tactac                                                              1866
```

<210> SEQ ID NO 9
<211> LENGTH: 622
<212> TYPE: PRT
<213> ORGANISM: Artificial
<220> FEATURE:
<223> OTHER INFORMATION: Synthetic

<400> SEQUENCE: 9

-continued

```
Met Arg Lys Leu Tyr Cys Val Leu Leu Leu Ser Ala Phe Glu Phe Thr
 1               5                  10                  15

Tyr Met Ile Asn Phe Gly Arg Gly Gln Asn Tyr Trp Glu His Pro Tyr
                20                  25                  30

Gln Asn Ser Asp Val Tyr Arg Pro Ile Asn Glu His Arg Glu His Pro
             35                  40                  45

Lys Glu Tyr Glu Tyr Pro Leu His Gln Glu His Thr Tyr Gln Gln Glu
         50                  55                  60

Asp Ser Gly Glu Asp Glu Asn Thr Leu Gln His Ala Tyr Pro Ile Asp
 65                  70                  75                  80

His Glu Gly Ala Glu Pro Ala Pro Gln Glu Gln Asn Leu Phe Ser Ser
                 85                  90                  95

Ile Glu Ile Val Glu Arg Ser Asn Tyr Met Gly Asn Pro Trp Thr Glu
                100                 105                 110

Tyr Met Ala Lys Tyr Asp Ile Glu Glu Val His Gly Ser Gly Ile Arg
             115                 120                 125

Val Asp Leu Gly Glu Asp Ala Glu Val Ala Gly Thr Gln Tyr Arg Leu
130                 135                 140

Pro Ser Gly Lys Cys Pro Val Phe Gly Lys Gly Ile Ile Ile Glu Asn
145                 150                 155                 160

Ser Lys Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
             180                 185                 190

Met Thr Leu Asp Glu Met Arg His Phe Tyr Lys Asp Asn Lys Tyr Val
             195                 200                 205

Lys Asn Leu Asp Glu Leu Thr Leu Cys Ser Arg His Ala Gly Asn Met
210                 215                 220

Ile Pro Asp Asn Asp Lys Asn Ser Asn Tyr Lys Tyr Pro Ala Val Tyr
225                 230                 235                 240

Asp Asp Lys Asp Lys Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
             260                 265                 270

Met Phe Cys Phe Arg Pro Ala Lys Asp Ile Ser Phe Gln Asn Leu Val
         275                 280                 285

Tyr Leu Ser Lys Asn Val Val Asp Asn Trp Glu Lys Val Cys Pro Arg
     290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
             340                 345                 350

Tyr Glu Gln His Leu Thr Asp Tyr Glu Lys Ile Lys Glu Gly Phe Lys
         355                 360                 365

Asn Lys Asn Arg Glu Met Ile Lys Ser Ala Phe Leu Pro Thr Gly Ala
     370                 375                 380

Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
                405                 410                 415
```

```
Thr Cys Leu Ile Asn Asp Lys Asn Tyr Ile Ala Thr Ala Leu Ser
        420                 425                 430

His Pro Ile Glu Val Glu Asn Asn Phe Pro Cys Ser Leu Tyr Lys Asp
435                 440                 445

Glu Ile Met Lys Glu Ile Glu Arg Glu Ser Lys Arg Ile Lys Leu Asn
        450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
                485                 490                 495

Val Ser Gln Ser Thr Cys Arg Phe Phe Val Cys Lys Cys Val Glu Arg
            500                 505                 510

Arg Ala Glu Val Thr Ser Asn Asn Glu Val Val Lys Glu Glu Tyr
        515                 520                 525

Lys Asp Glu Tyr Ala Asp Ile Pro Glu His Lys Pro Thr Tyr Asp Lys
        530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
                565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Lys Arg
        595                 600                 605

Ala Ser His Thr Thr Pro Val Leu Met Glu Lys Pro Tyr Tyr
    610                 615                 620

<210> SEQ ID NO 10
<211> LENGTH: 1071
<212> TYPE: DNA
<213> ORGANISM: Artificial
<220> FEATURE:
<223> OTHER INFORMATION: Synthetic

<400> SEQUENCE: 10
atgatgcgca agctggccat cctgtccgtg tcctccttcc tgttcgtgga ggccctgttc      60
caggagtacc agtgctacgg ctcctcctcc aacacccgcg tgctgaacga gctgaactac     120
gacaacgccg gcaccaacct gtacaacgag ctggagatga actactacgg caagcaggag     180
aactggtact ccctgaagaa gaactcccgc tccctgggcg agaacgacga cggcaacaac     240
gaggacaacg agaagctgcg caagcccaag cacaagaagc tgaagcagcc cgccgacggc     300
aaccccgacc caacgccaa ccccaacgtg gaccccaacg ccaaccccaa cgtggacccc     360
aacgccaacc caacgtgga ccccaacgcc aaccccaacg ccaaccccaa cgccaacccc     420
aacgccaacc caacgccaa ccccaacgcc aaccccaacg ccaaccccaa cgccaacccc     480
aacgccaacc caacgccaa ccccaacgcc aaccccaacg ccaaccccaa cgccaacccc     540
aacgccaacc caacgccaa ccccaacgcc aaccccaacg ccaaccccaa cgtggacccc     600
aacgccaacc caacgccaa ccccaacaag aacaaccagg gcaacggcca gggccacaac     660
atgcccaacg accccaaccg caacgtggac gagaacgcca cgccaactc cgccgtgaag     720 aacaacaaca cgaggagcc ctccgacaag cacatcaagg agtacctgaa caagatccag     780
aactccctgt ccaccgagtg gtccccctgt ccgtgacct gcggcaacgg catccaggtg     840
cgcatcaagc ccggctccgc caacaagccc aaggacgagc tggactacgc caacgacatc     900
```

```
gagaagaaga tctgcaagat ggagaagtgc tcctccgtgt tcaacgtggt gaactcctcc    960
atcggcctga tcatggtgct gtccttcctg ttcctgaacg aattcgatga tctgctgtgc   1020
cttctagttg ccagccatct gttgtttgcc cctcccccgt gccttcctta a             1071
```

<210> SEQ ID NO 11
<211> LENGTH: 356
<212> TYPE: PRT
<213> ORGANISM: Artificial
<220> FEATURE:
<223> OTHER INFORMATION: Synthetic

<400> SEQUENCE: 11

```
Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Lys Asn Asn Gln Gly Asn Gly Gln Gly His Asn Met Pro Asn Asp
    210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
                245                 250                 255

Asn Lys Ile Gln Asn Ser Leu Ser Thr Glu Trp Ser Pro Cys Ser Val
            260                 265                 270

Thr Cys Gly Asn Gly Ile Gln Val Arg Ile Lys Pro Gly Ser Ala Asn
        275                 280                 285

Lys Pro Lys Asp Glu Leu Asp Tyr Ala Asn Asp Ile Glu Lys Lys Ile
    290                 295                 300

Cys Lys Met Glu Lys Cys Ser Ser Val Phe Asn Val Asn Ser Ser
305                 310                 315                 320

Ile Gly Leu Ile Met Val Leu Ser Phe Leu Phe Leu Asn Glu Phe Asp
                325                 330                 335
```

Asp Leu Leu Cys Leu Leu Val Ala Ser His Leu Phe Ala Pro Pro
            340                 345                 350

Pro Cys Leu Pro
        355

<210> SEQ ID NO 12
<211> LENGTH: 999
<212> TYPE: DNA
<213> ORGANISM: Artificial
<220> FEATURE:
<223> OTHER INFORMATION: Synthetic

<400> SEQUENCE: 12
atgatgcgca agctggccat cctgtccgtg tcctccttcc tgttcgtgga ggccctgttc      60
caggagtacc agtgctacgg ctcctcctcc aacacccgcg tgctgaacga gctgaactac     120
gacaacgccg gcaccaacct gtacaacgag ctggagatga actactacgg caagcaggag     180
aactggtact ccctgaagaa gaactcccgc tccctgggcg agaacgacga cggcaacaac     240
gaggacaacg agaagctgcg caagcccaag cacaagaagc tgaagcagcc cgccgacggc     300
aaccccgacc ccaacgccaa ccccaacgtg gaccccaacg ccaaccccaa cgtggacccc     360
aacgccaacc ccaacgtgga ccccaacgcc aaccccaacg ccaaccccaa cgccaacccc     420
aacgccaacc ccaacgccaa ccccaacgcc aaccccaacg ccaaccccaa cgccaacccc     480
aacgccaacc ccaacgccaa ccccaacgcc aaccccaacg ccaaccccaa cgccaacccc     540
aacgccaacc ccaacgccaa ccccaacgcc aaccccaacg ccaaccccaa cgccaacccc     600
aacgccaacc ccaacgccaa ccccaacaag aacaaccagg gcaacggcca gggccacaac     660
atgcccaacg accccaaccg caacgtggac gagaacgcca cgccaactc cgccgtgaag      720 aacaacaaca cgaggagcc ctccgacaag cacatcaagg agtacctgaa caagatccag      780
aactccctgt ccaccgagtg gtcccccctgc tccgtgacct gcggcaacgg catccaggtg    840
cgcatcaagc ccggctccgc caacaagccc aaggacgagc tggactacgc caacgacatc     900
gagaagaaga tctgcaagat ggagaagtgc tcctccgtgt tcaacgtggt gaactcctcc     960
atcggcctga tcatggtgct gtccttcctg ttcctgaac                            999

<210> SEQ ID NO 13
<211> LENGTH: 333
<212> TYPE: PRT
<213> ORGANISM: Artificial
<220> FEATURE:
<223> OTHER INFORMATION: Synthetic

<400> SEQUENCE: 13

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
            20                  25                  30

Arg Val Leu Asn Glu Leu Asn Tyr Asp Asn Ala Gly Thr Asn Leu Tyr
        35                  40                  45

Asn Glu Leu Glu Met Asn Tyr Tyr Gly Lys Gln Glu Asn Trp Tyr Ser
    50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro

```
            100                 105                 110
Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
            165                 170                 175

Asn Ala Asn Pro Asn Ala Asn Pro Asn Ala Asn Pro Asn Ala Asn Pro
        180                 185                 190

Asn Ala Asn Pro Asn Val Asp Pro Asn Ala Asn Pro Asn Ala Asn Pro
    195                 200                 205

Asn Lys Asn Asn Gln Gly Asn Gly Gln Gly His Asn Met Pro Asn Asp
210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
            245                 250                 255

Asn Lys Ile Gln Asn Ser Leu Ser Thr Glu Trp Ser Pro Cys Ser Val
        260                 265                 270

Thr Cys Gly Asn Gly Ile Gln Val Arg Ile Lys Pro Gly Ser Ala Asn
    275                 280                 285

Lys Pro Lys Asp Glu Leu Asp Tyr Ala Asn Asp Ile Glu Lys Lys Ile
290                 295                 300

Cys Lys Met Glu Lys Cys Ser Ser Val Phe Asn Val Val Asn Ser Ser
305                 310                 315                 320

Ile Gly Leu Ile Met Val Leu Ser Phe Leu Phe Leu Asn
            325                 330
```

<210> SEQ ID NO 14
<211> LENGTH: 969
<212> TYPE: DNA
<213> ORGANISM: Artificial
<220> FEATURE:
<223> OTHER INFORMATION: Synthetic

<400> SEQUENCE: 14

```
atgatgcgca agctggccat cctgtccgtg tcctccttcc tgttcgtgga ggccctgttc      60
caggagtacc agtgctacgg ctcctcctcc aacacccgcg tgctgaacga gctgaactac     120
gacaacgccg gcaccaacct gtacaacgag ctggagatga actactacgg caagcaggag     180
aactggtact ccctgaagaa gaactcccgc tccctgggcg agaacgacga cggcaacaac     240
gaggacaacg agaagctgcg caagcccaag cacaagaagc tgaagcagcc cgccgacggc     300
aaccccgacc ccaacgccaa ccccaacgtg gaccccaacg ccaaccccaa cgtggacccc     360
aacgccaacc ccaacgtgga ccccaacgcc aaccccaacg ccaaccccaa cgccaacccc     420
aacgccaacc ccaacgccaa ccccaacgcc aaccccaacg ccaaccccaa cgccaacccc     480
aacgccaacc ccaacgccaa ccccaacgcc aaccccaacg ccaaccccaa cgccaacccc     540
aacgccaacc ccaacgccaa ccccaacgcc aaccccaacg ccaaccccaa cgtggacccc     600
aacgccaacc ccaacgccaa ccccaacaag aacaaccagg gcaacggcca gggccacaac     660
atgcccaacg accccaaccg caacgtggac gagaacgcca acgccaactc cgccgtgaag     720
aacaacaaca acgaggagcc ctccgacaag cacatcaagg agtacctgaa caagatccag     780
```

```
aactccctgt ccaccgagtg gtcccctgc tccgtgacct gcggcaacgg catccaggtg    840
cgcatcaagc ccggctccgc caacaagccc aaggacgagc tggactacgc caacgacatc    900
gagaagaaga tctgcaagat ggagaagtgc tcctccgtgt tcaacgtggt gaactcctcc    960
atcggctaa                                                            969
```

<210> SEQ ID NO 15
<211> LENGTH: 322
<212> TYPE: PRT
<213> ORGANISM: Artificial
<220> FEATURE:
<223> OTHER INFORMATION: Synthetic

<400> SEQUENCE: 15

```
Met Met Arg Lys Leu Ala Ile Leu Ser Val Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
50                  55                  60

Leu Lys Lys Asn Ser Arg Ser Leu Gly Glu Asn Asp Asp Gly Asn Asn
65                  70                  75                  80

Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Lys Asn Asn Gln Gly Asn Gly Gln Gly His Asn Met Pro Asn Asp
    210                 215                 220

Pro Asn Arg Asn Val Asp Glu Asn Ala Asn Ala Asn Ser Ala Val Lys
225                 230                 235                 240

Asn Asn Asn Asn Glu Glu Pro Ser Asp Lys His Ile Lys Glu Tyr Leu
                245                 250                 255

Asn Lys Ile Gln Asn Ser Leu Ser Thr Glu Trp Ser Pro Cys Ser Val
            260                 265                 270

Thr Cys Gly Asn Gly Ile Gln Val Arg Ile Lys Pro Gly Ser Ala Asn
        275                 280                 285

Lys Pro Lys Asp Glu Leu Asp Tyr Ala Asn Asp Ile Glu Lys Lys Ile
    290                 295                 300

Cys Lys Met Glu Lys Cys Ser Ser Val Phe Asn Val Val Asn Ser Ser
305                 310                 315                 320
```

Ile Gly

<210> SEQ ID NO 16
<211> LENGTH: 1869
<212> TYPE: DNA
<213> ORGANISM: Artificial
<220> FEATURE:
<223> OTHER INFORMATION: Synthetic

<400> SEQUENCE: 16

```
atgcgcaagc tgtactgcgt gctgctgctg tccgccttcg agttcaccta catgatcaac      60
ttcggccgcg ccagaactac tgggagcac ccctaccaga actccgacgt gtaccgcccc     120
atcaacgagc accgcgagca ccccaaggag tacgagtacc cctgcaccag gagcacacc     180
taccagcagg aggactccgg cgaggacgag aacaccctgc agcacgccta ccccatcgac     240
cacgagggcg ccgagcccgc ccccaaggag cagaacctgt tctcctccat cgagatcgtg     300
gagcgctcca actacatggg caaccccctgg accgagtaca tggccaagta cgacatcgag     360
gaggtgcacg gctccggcat ccgcgtggac ctgggcgagg acgccgaggt ggccggcacc     420
cagtaccgcc tgccctccgg caagtgcccc gtgttcggca agggcatcat catcgagaac     480
tccaacacca ccttcctgac ccccgtggcc accggcaacc agtacctgaa ggacggcggc     540
ttcgccttcc ccccaccga gccctgatg tccccatga ccctggacga gatgcgccac         600
ttctacaaga caacaagta cgtgaagaac ctggacgagc tgaccctgtg ctcccgccac       660
gccggcaaca tgatccccga caacgacaag aactccaact acaagtaccc cgccgtgtac     720
gacgacaagg acaagaagtg ccacatcctg tacatcgccg cccaggagaa caacggcccc     780
cgctactgca acaaggacga gtccaagcgc aactccatgt tctgcttccg ccccgccaag     840
gacatctcct tccagaacta cacctacctg tccaagaacg tggtggacaa ctgggagaag     900
gtgtgccccc gcaagaacct gcagaacgcc aagttcggcc tgtgggtgga cggcaactgc     960
gaggacatcc cccacgtgaa cgagttcccc gccatcgacc tgttcgagtg caacaagctg    1020
gtgttcgagc tgtccgcctc cgaccagccc aagcagtacg agcagcacct gaccgactac    1080
gagaagatca ggagggcttc aagaacaag aacgcctcca tgatcaagtc cgccttcctg     1140
cccaccggcg ccttcaaggc cgaccgctac aagtcccacg caagggcta caactggggc     1200
aactacaaca ccgagaccca gaagtgcgag atcttcaacg tgaagcccac ctgcctgatc    1260
aacaactcct cctacatcgc caccaccgcc ctgtcccacc catcgaggt ggagaacaac       1320
ttcccctgct ccctgtacaa ggacgagatc atgaaggaga tcgagcgcga gtccaagcgc    1380
atcaagctga cgacaacga cgacgagggc aacaagaaga tcatcgcccc cgcatcttc      1440
atctccgacg acaaggactc cctgaagtgc cctgcgacc ccgagatggt gtccaactcc      1500
acctgccgct tcttcgtgtg caagtgcgtg gagcgccgcg ccgaggtgac ctccaacaac    1560
gaggtggtgg tgaaggagga gtacaaggac gagtacgccg acatcccga gcacaagccc      1620
acctacgaca agatgaagat catcatcgcc tcctccgccg ccgtggccgt gctggccacc    1680
atcctgatgg tgtacctgta caagcgcaag ggcaacgccg agaagtacga caagatggac    1740
gagccccagg actacggcaa gtccaactcc cgcaacgacg agatgctgga ccccgaggcc    1800
tccttctggg gcgaggagaa gcgcgcctcc cacaccaccc ccgtgctgat ggagaagccc    1860
tactactaa                                                            1869
```

<210> SEQ ID NO 17
<211> LENGTH: 622

<212> TYPE: PRT
<213> ORGANISM: Artificial
<220> FEATURE:
<223> OTHER INFORMATION: Synthetic

<400> SEQUENCE: 17

Met Arg Lys Leu Tyr Cys Val Leu Leu Leu Ser Ala Phe Glu Phe Thr
1               5                   10                  15

Tyr Met Ile Asn Phe Gly Arg Gly Gln Asn Tyr Trp Glu His Pro Tyr
            20                  25                  30

Gln Asn Ser Asp Val Tyr Arg Pro Ile Asn Glu His Arg Glu His Pro
        35                  40                  45

Lys Glu Tyr Glu Tyr Pro Leu His Gln Glu His Thr Tyr Gln Gln Glu
50                  55                  60

Asp Ser Gly Glu Asp Glu Asn Thr Leu Gln His Ala Tyr Pro Ile Asp
65                  70                  75                  80

His Glu Gly Ala Glu Pro Ala Pro Gln Glu Gln Asn Leu Phe Ser Ser
                85                  90                  95

Ile Glu Ile Val Glu Arg Ser Asn Tyr Met Gly Asn Pro Trp Thr Glu
            100                 105                 110

Tyr Met Ala Lys Tyr Asp Ile Glu Glu Val His Gly Ser Gly Ile Arg
        115                 120                 125

Val Asp Leu Gly Glu Asp Ala Glu Val Ala Gly Thr Gln Tyr Arg Leu
130                 135                 140

Pro Ser Gly Lys Cys Pro Val Phe Gly Lys Gly Ile Ile Ile Glu Asn
145                 150                 155                 160

Ser Asn Thr Thr Phe Leu Thr Pro Val Ala Thr Gly Asn Gln Tyr Leu
                165                 170                 175

Lys Asp Gly Gly Phe Ala Phe Pro Pro Thr Glu Pro Leu Met Ser Pro
            180                 185                 190

Met Thr Leu Asp Glu Met Arg His Phe Tyr Lys Asp Asn Lys Tyr Val
        195                 200                 205

Lys Asn Leu Asp Glu Leu Thr Leu Cys Ser Arg His Ala Gly Asn Met
210                 215                 220

Ile Pro Asp Asn Asp Lys Asn Ser Asn Tyr Lys Tyr Pro Ala Val Tyr
225                 230                 235                 240

Asp Asp Lys Asp Lys Lys Cys His Ile Leu Tyr Ile Ala Ala Gln Glu
                245                 250                 255

Asn Asn Gly Pro Arg Tyr Cys Asn Lys Asp Glu Ser Lys Arg Asn Ser
            260                 265                 270

Met Phe Cys Phe Arg Pro Ala Lys Asp Ile Ser Phe Gln Asn Tyr Thr
        275                 280                 285

Tyr Leu Ser Lys Asn Val Val Asp Asn Trp Glu Lys Val Cys Pro Arg
290                 295                 300

Lys Asn Leu Gln Asn Ala Lys Phe Gly Leu Trp Val Asp Gly Asn Cys
305                 310                 315                 320

Glu Asp Ile Pro His Val Asn Glu Phe Pro Ala Ile Asp Leu Phe Glu
                325                 330                 335

Cys Asn Lys Leu Val Phe Glu Leu Ser Ala Ser Asp Gln Pro Lys Gln
            340                 345                 350

Tyr Glu Gln His Leu Thr Asp Tyr Glu Lys Ile Lys Glu Gly Phe Lys
        355                 360                 365

Asn Lys Asn Ala Ser Met Ile Lys Ser Ala Phe Leu Pro Thr Gly Ala
370                 375                 380

```
Phe Lys Ala Asp Arg Tyr Lys Ser His Gly Lys Gly Tyr Asn Trp Gly
385                 390                 395                 400

Asn Tyr Asn Thr Glu Thr Gln Lys Cys Glu Ile Phe Asn Val Lys Pro
            405                 410                 415

Thr Cys Leu Ile Asn Asn Ser Ser Tyr Ile Ala Thr Thr Ala Leu Ser
            420                 425                 430

His Pro Ile Glu Val Glu Asn Asn Phe Pro Cys Ser Leu Tyr Lys Asp
            435                 440                 445

Glu Ile Met Lys Glu Ile Glu Arg Glu Ser Lys Arg Ile Lys Leu Asn
            450                 455                 460

Asp Asn Asp Asp Glu Gly Asn Lys Lys Ile Ile Ala Pro Arg Ile Phe
465                 470                 475                 480

Ile Ser Asp Asp Lys Asp Ser Leu Lys Cys Pro Cys Asp Pro Glu Met
            485                 490                 495

Val Ser Asn Ser Thr Cys Arg Phe Phe Val Cys Lys Cys Val Glu Arg
            500                 505                 510

Arg Ala Glu Val Thr Ser Asn Asn Glu Val Val Val Lys Glu Glu Tyr
            515                 520                 525

Lys Asp Glu Tyr Ala Asp Ile Pro Glu His Lys Pro Thr Tyr Asp Lys
            530                 535                 540

Met Lys Ile Ile Ile Ala Ser Ser Ala Ala Val Ala Val Leu Ala Thr
545                 550                 555                 560

Ile Leu Met Val Tyr Leu Tyr Lys Arg Lys Gly Asn Ala Glu Lys Tyr
            565                 570                 575

Asp Lys Met Asp Glu Pro Gln Asp Tyr Gly Lys Ser Asn Ser Arg Asn
            580                 585                 590

Asp Glu Met Leu Asp Pro Glu Ala Ser Phe Trp Gly Glu Glu Lys Arg
            595                 600                 605

Ala Ser His Thr Thr Pro Val Leu Met Glu Lys Pro Tyr Tyr
            610                 615                 620
```

ADENOVIRAL VECTOR-BASED MALARIA VACCINES

STATEMENT REGARDING FEDERALLY SPONSORED RESEARCH AND DEVELOPMENT

This invention was made in part with Government support under Cooperative Research and Development Agreement (CRADA) Number NMR-04-1869, and amendments thereto, executed between GenVec, Inc. and the Naval Medical Research Center (NMRC). The Government may have certain rights in this invention.

CROSS-REFERENCE TO RELATED APPLICATIONS

This application is a divisional application of U.S. application Ser. No. 12/522,335, filed Jun. 11, 2010, which is the national stage application of PCT Application No. PCT/US2008/050565, filed Jan. 9, 2008, which claims the benefit of U.S. Provisional Patent Application No. 60/884,126, filed Jan. 9, 2007, which is incorporated by reference.

SEQUENCE LISTING

Incorporated by reference in its entirety herein is a computer-readable nucleotide/amino acid sequence listing submitted concurrently herewith and identified as follows: One (1) 45,ee4 byte I\SCII (Tent) file aamea "7Q2374_ST25.TXT," eFeatea en Jan. 8, 2008 45,549 Byte ASCII (Text) file named "705154_ST25.txt." created on Jul. 7, 2009.

BACKGROUND OF THE INVENTION

Malaria is one of the most devastating parasitic diseases affecting humans. Indeed, 41% of the world's population lives in areas where malaria is transmitted (e.g., parts of Africa, Asia, the Middle East, Central and South America, Hispaniola, and Oceania). The World Health Organization (WHO) and the Centers for Disease Control (CDC) estimate that malaria infects 300-500 million people and kills 700,000-3 million people annually, with the majority of deaths occurring in children in sub-Saharan Africa. Malaria also is a major health concern to U.S. military personnel deployed to tropical regions of the world. For example, in August 2003, 28% of the 26th Marine Expeditionary Unit and Joint Task Force briefly deployed to Monrovia, Liberia, were infected with the malaria parasite *Plasmodium falciparum*. In addition, one 157-man Marine Expeditionary Unit sustained a 44% malaria casualty rate over a 12-day period while stationed at Robert International Airport in Monrovia. In all conflicts during the past century conducted in malaria endemic areas, malaria has been the leading cause of casualties, exceeding enemy-inflicted casualties in its impact on "person-days" lost from duty.

To combat malaria during U.S. military operations, preventive drugs, insect repellants, and barriers have been used with some success, but developing drug resistance by the malaria parasite and insecticide resistance by mosquito vectors has limited the efficacy of these agents. Moreover, the logistical burden and side effects associated with the use of these agents often is associated with high non-compliance rates. Vaccines are the most cost effective and efficient therapeutic interventions for infectious diseases. In this regard, vaccination has the advantage of administration prior to military deployment and likely reduction in non-compliance risks. However, decades of research and development directed to a malaria vaccine have not proven successful. Recent efforts have focused on developing vaccines against several specific malaria genes and delivery vector systems including adenovirus, poxvirus, and plasmids. The current status of malaria vaccine development and clinical trials is reviewed in, for example, Graves and Gelband, *Cochrane Database Syst. Rev.*, 1: CD000129 (2003), Moore et al., *Lancet Infect. Dis.*, 2: 737-743 (2002), Carvalho et al., *Scand. J. Immunol.*, 56: 327-343 (2002), Moorthy and Hill, *Br. Med. Bull.*, 62: 59-72 (2002), Greenwood and Alonso, *Chem. Immunol.*, 80: 366-395 (2002), and Richie and Saul, *Nature*, 415: 694-701 (2002).

Over the past 15-20 years, a series of Phase 1/2 vaccine trials have been reported using synthetic peptides or recombinant proteins based on malarial antigens. Approximately 40 trials were reported as of 1998 (see Engers and Godal, *Parisitology Today*, 14: 56-64 (1998)). Most of these trials have been directed against the sporozoite stage or liver stage of the *Plasmodium* life cycle, where the use of experimental mosquito challenges allows rapid progress through Phase 1 to Phase 2a preliminary efficacy studies. Anti-sporozoite vaccines tested include completely synthetic peptides, conjugates of synthetic peptide with proteins such as tetanus toxoid (to provide T cell help), recombinant malaria proteins, particle-forming recombinant chimeric constructs, recombinant viruses, and bacteria and DNA vaccines. Several trials of asexual blood stage vaccines have used either synthetic peptide conjugates or recombinant proteins. There also has been a single trial of a transmission blocking vaccine (recombinant Pfs25). A recurring problem identified in all of these vaccination strategies is the difficulty in obtaining a sufficiently strong and long lasting immune response in humans, despite the strong immunogenic response in animal models.

To overcome these limitations, the development of potent immune-stimulatory conjugates or adjuvants to boost the human response has been explored, in addition to the development of vaccines directed against the circumsporozoite protein (CSP), which is the principal sporozoite coat protein. Anti-CSP vaccines using recombinant proteins, peptide conjugates, recombinant protein conjugates, and chimeric proteins have been shown to elicit anti-CSP antibodies. Although considerable efforts are still being directed at the development of protein-based vaccines, alternative technologies such as DNA and viral based vaccines have shown some promise with regard to immunogenicity and protective efficacy, at least in animal models.

In this regard, DNA vaccines encoding *Plasmodium* antigens have been developed and can induce CD8+ CTL and IFN-γ responses, as well as protection against sporozoite challenge in mice (see Sedegah et al., *Proc. Natl. Acad. Sci. USA*, 91: 9866-9870 (1994), and Doolan et al., *J. Exp. Med.*, 183: 1739-1746 (1996)) and monkeys (Wang et al., *Science*, 282: 476-480 (1998), Rogers et al., *Infect. Immun.*, 69: 5565-5572 (2001), and Rogers et al., *Infect. Immun.*, 70: 4329-4335 (2002)). Furthermore, Phase I and Phase 2a clinical trials have established the safety, tolerability, and immunogenicity of DNA vaccines encoding malaria antigens in normal healthy humans (see, e.g., Wang et al., *Infect Immun.*, 66: 4193-41202 (1998), Le et al., *Vaccine*, 18: 1893-1901 (2000), and Epstein et al., *Hum. Gene Ther.*, 13: 1551-1560 (2002)). However, the immunogenicity of first and second-generation DNA vaccines in nonhuman primates and in humans has been suboptimal. Even in murine models, DNA vaccines are not effective at activating both arms of the immune system (see, e.g., Doolan et al., supra, Sedegah et al., supra, Sedegah et al.,

*Proc. Natl. Acad. Sci. USA*, 95: 7648-7653 (1998), Zavala et al., *Virology*, 280: 155-159 (2001), and Pardoll, *Nat. Rev. Immunol*, 2: 227-238 (2002)).

Thus, there remains a need for improved methods that effectively deliver malaria antigens to human hosts so as to prevent the onset of disease and/or protect human hosts from further infections. The invention provides such methods. This and other advantages of the invention will become apparent from the detailed description provided herein.

BRIEF SUMMARY OF THE INVENTION

The invention provides a method of inducing an immune response against malaria in a mammal. The method comprises intramuscularly administering to a mammal a composition comprising a pharmaceutically acceptable carrier and either or both of (a) about $1\times10^6$ particle units (pu) to about $1\times10^{12}$ pu of a first adenoviral vector comprising an adenoviral genome comprising a left inverted terminal repeat (ITR), the E2A region, the E2B region, late regions L1-L5, and a right ITR, and a nucleic acid sequence encoding a *P. falciparum* circumsporozoite protein (CSP) operably linked to a human CMV promoter, and/or (b) about $1\times10^6$ particle units pu to about $1\times10^{12}$ pu of a second adenoviral vector comprising an adenoviral genome comprising a left inverted terminal repeat (ITR), the E2A region, the E2B region, late regions L1-L5, and a right ITR, and a nucleic acid sequence encoding a *P. falciparum* apical membrane antigen 1 (AMA-1) antigen operably linked to a human CMV promoter. The composition is administered to the mammal one or more times, and the nucleic acid sequence encoding a *P. falciparum* CSP and/or the nucleic acid sequence encoding a *P. falciparum* AMA-1 are expressed to produce the CSP and/or the AMA-1 in the mammal to induce an immune response against malaria.

DETAILED DESCRIPTION OF THE INVENTION

The development of a single vaccine that immunizes a host against multiple antigens of a single pathogen and protects against pathogen challenge (i.e., a "multivalent" vaccine) provides a number of advantages over current vaccine methodologies. In particular, multivalent vaccines induce more potent and broad host responses against a given pathogen, and are a more cost-effective alternative to the preparation and administration of multiple vaccines that target a single pathogen. Thus, the invention provides a method of inducing an immune response against malaria in a mammal. The method comprises intramuscularly administering to a mammal a composition comprising a pharmaceutically acceptable carrier and either or both of (a) about $1\times10^6$ particle units (pu) to about $1\times10^{12}$ pu of a first adenoviral vector comprising an adenoviral genome comprising a left inverted terminal repeat (ITR), the E2A region, the E2B region, late regions L1-L5, and a right ITR, and a nucleic acid sequence encoding a *P. falciparum* circumsporozoite protein (CSP) operably linked to a human CMV promoter, and/or (b) about $1\times10^6$ particle units pu to about $1\times10^{12}$ pu of a second adenoviral vector comprising an adenoviral genome comprising a left inverted terminal repeat (ITR), the E2A region, the E2B region, late regions L1-L5, and a right ITR, and a nucleic acid sequence encoding a *P. falciparum* apical membrane antigen 1 (AMA-1) antigen operably linked to a human CMV promoter. The composition is administered to the mammal one or more times, and the nucleic acid sequence encoding a *P. falciparum* CSP and/or the nucleic acid sequence encoding a *P. falciparum* AMA-1 are expressed to produce the CSP and/or the AMA-1 in the mammal to induce an immune response against malaria.

Adenovirus (Ad) is a 36 kb double-stranded DNA virus that efficiently transfers DNA in vivo to a variety of different target cell types. For use in the invention, the adenovirus is preferably made replication-deficient by deleting, in whole or in part, select genes required for viral replication. The expendable E3 region is also frequently deleted to allow additional room for a larger DNA insert. The vector can be produced in high titers and can efficiently transfer DNA to replicating and non-replicating cells. The newly transferred genetic information remains epi-chromosomal, thereby eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors can be a desirable option for use in the invention.

Adenovirus from various origins, subtypes, or mixture of subtypes can be used as the source of the viral genome for the adenoviral vector. While non-human adenovirus (e.g., simian, avian, canine, ovine, or bovine adenoviruses) can be used to generate the adenoviral vector, a human adenovirus preferably is used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 97/12986 and WO 98/53087.

The adenoviral vector can comprise a mixture of subtypes and thereby be a "chimeric" adenoviral vector. A chimeric adenoviral vector can comprise an adenoviral genome that is derived from two or more (e.g., 2, 3, 4, etc.) different adenovirus serotypes. In the context of the invention, a chimeric adenoviral vector can comprise approximately different or equal amounts of the genome of each of the two or more different adenovirus serotypes. When the chimeric adenoviral vector genome is comprised of the genomes of two different adenovirus serotypes, the chimeric adenoviral vector genome preferably comprises no more than about 70% (e.g., no more than about 65%, about 50%, or about 40%) of the genome of one of the adenovirus serotypes, with the remainder of the chimeric adenovirus genome being derived from the genome of the other adenovirus serotype. In one embodiment, the chimeric adenoviral vector can contain an adenoviral genome comprising a portion of a serotype 2 genome and a portion of a serotype 5 genome. For example, nucleotides 1-456 of such an adenoviral vector can be derived from a serotype 2 genome, while the remainder of the adenoviral genome can be derived from a serotype 5 genome.

By "replication-deficient" is meant that the adenoviral vector requires complementation of one or more regions of the adenoviral genome that are required for replication, as a result of, for example, a deficiency in at least one replication-essential gene function (i.e., such that the adenoviral vector does not replicate in typical host cells, especially those in a human patient that could be infected by the adenoviral vector in the course of the inventive method). A deficiency in a gene, gene function, gene, or genomic region, as used herein, is defined as a mutation or deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was mutated or deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2).

The replication-deficient adenoviral vector desirably requires complementation of at least one replication-essential gene function of one or more regions of the adenoviral genome for viral replication. Preferably, the adenoviral vector requires complementation of at least one gene function of the E1A region, the E1B region, or the E4 region of the adenoviral genome required for viral replication (denoted an E1-deficient or E4-deficient adenoviral vector). In addition to a deficiency in the E1 region, the recombinant adenovirus also can have a mutation in the major late promoter (MLP), as discussed in International Patent Application Publication WO 00/00628. Most preferably, the adenoviral vector is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenoviral vector can be deficient in part or all of the E1A region and/or part or all of the E1B region, e.g., in at least one replication-essential gene function of each of the E1A and E1B regions, thus requiring complementation of the E1A region and the E1B region of the adenoviral genome for replication. The adenoviral vector also can require complementation of the E4 region of the adenoviral genome for replication, such as through a deficiency in one or more replication-essential gene functions of the E4 region.

When the adenoviral vector is E1-deficient, the adenoviral vector genome can comprise a deletion beginning at any nucleotide between nucleotides 335 to 375 (e.g., nucleotide 356) and ending at any nucleotide between nucleotides 3,310 to 3,350 (e.g., nucleotide 3,329) or even ending at any nucleotide between 3,490 and 3,530 (e.g., nucleotide 3,510) (based on the adenovirus serotype 5 genome). When E3-deficient, the adenoviral vector genome can comprise a deletion beginning at any nucleotide between nucleotides 28,575 to 29,615 (e.g., nucleotide 28,593) and ending at any nucleotide between nucleotides 30,450 to 30,490 (e.g., nucleotide 30,470) (based on the adenovirus serotype 5 genome). When E4-deficient, the adenoviral vector genome can comprise a deletion beginning at, for example, any nucleotide between nucleotides 32,805 to 32,845 (e.g., nucleotide 32,826) and ending at, for example, any nucleotide between nucleotides 35,540 to 35,580 (e.g., nucleotide 35,561) (based on the adenovirus serotype 5 genome). The endpoints defining the deleted nucleotide portions can be difficult to precisely determine and typically will not significantly affect the nature of the adenoviral vector, i.e., each of the aforementioned nucleotide numbers can be +/−1, 2, 3, 4, 5, or even 10 or 20 nucleotides.

When the adenoviral vector is deficient in at least one replication-essential gene function in one region of the adenoviral genome (e.g., an E1- or E1/E3-deficient adenoviral vector), the adenoviral vector is referred to as "singly replication-deficient." A particularly preferred singly replication-deficient adenoviral vector is, for example, a replication-deficient adenoviral vector requiring, at most, complementation of the E1 region of the adenoviral genome, so as to propagate the adenoviral vector (e.g., to form adenoviral vector particles).

The adenoviral vector can be "multiply replication-deficient," meaning that the adenoviral vector is deficient in one or more replication-essential gene functions in each of two or more regions of the adenoviral genome, and requires complementation of those functions for replication. For example, the aforementioned E1-deficient or E1/E3-deficient adenoviral vector can be further deficient in at least one replication-essential gene function of the E4 region (denoted an E1/E4- or E1/E3/E4-deficient adenoviral vector). When the adenoviral vector is multiply replication-deficient, the deficiencies can be a combination of the nucleotide deletions discussed above with respect to each individual region.

While the above-described deletions are described with respect to an adenovirus serotype 5 genome, one of ordinary skill in the art can determine the nucleotide coordinates of the same regions of other adenovirus serotypes, such as an adenovirus serotype 2 genome, without undue experimentation, based on the similarity between the genomes of various adenovirus serotypes, particularly adenovirus serotypes 2 and 5.

In the inventive method, the first adenoviral vector and the second adenoviral vector each comprises an adenoviral genome comprising a left inverted terminal repeat (ITR), the E2A region, the E2B region, late regions L1-L5, and a right ITR. The adenoviral genome also is deficient in one or more replication-essential gene functions of each of the E1 and E4 regions (i.e., the adenoviral vector is an E1/E4-deficient adenoviral vector), preferably with the entire coding region of the E4 region having been deleted from the adenoviral genome. In other words, all the open reading frames (ORFs) of the E4 region have been removed. Most preferably, the adenoviral vector is rendered replication-deficient by deletion of all of the E1 region and by deletion of a portion of the E4 region. The E4 region of the adenoviral vector can retain the native E4 promoter, polyadenylation sequence, and/or the right-side inverted terminal repeat (ITR).

It should be appreciated that the deletion of different regions of an adenoviral vector can alter the immune response of the mammal. In particular, deletion of different regions can reduce the inflammatory response generated by the adenoviral vector. An adenoviral vector deleted of the entire E4 region can elicit a lower host immune response. Furthermore, the adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent disorders.

The adenoviral vector, when multiply replication-deficient, especially in replication-essential gene functions of the E1 and E4 regions, can include a spacer sequence to provide viral growth in a complementing cell line similar to that achieved by singly replication-deficient adenoviral vectors, particularly an E1-deficient adenoviral vector. In a preferred E4-deficient adenoviral vector of the invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication-deficient adenoviral vector, particularly a singly replication-deficient E1 deficient adenoviral vector.

The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer sequence can be coding or non-coding and native or non-native with respect to the adenoviral genome, but does not restore the replication-essential function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promoter is not present in the vector, the spacer is proximal to the right-side ITR. The spacer can comprise any suitable polyadenylation sequence. Examples of suitable polyadenylation sequences include synthetic optimized sequences, BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. Ideally, the spacer is composed of the glucuronidase gene. The use of a spacer in an adenoviral vector is further described in, for example, U.S. Pat. No. 5,851,806 and International Patent Application Publication WO 97/21826.

It has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others, as described in for example, U.S. Pat. Nos. 6,225,113, 6,649,373, and 6,660,521, and International Patent Application Publication WO 00/34496. In view of the above, a replication-deficient adenoviral vector (e.g., the at least E4-deficient adenoviral vector) or a second expression vector can comprise a nucleic acid sequence encoding a trans-acting factor that modulates the persistence of expression of the nucleic acid sequence.

Desirably, the adenoviral vector requires, at most, complementation of replication-essential gene functions of the E1 and/or E4 regions of the adenoviral genome for replication (i.e., propagation). However, the adenoviral genome can be modified to disrupt one or more replication-essential gene functions as desired by the practitioner, so long as the adenoviral vector remains deficient and can be propagated using, for example, complementing cells and/or exogenous DNA (e.g., helper adenovirus) encoding the disrupted replication-essential gene functions. Suitable replication-deficient adenoviral vectors, including singly and multiply replication-deficient adenoviral vectors, are disclosed in U.S. Pat. Nos. 5,837,511, 5,851,806, 5,994,106, 6,127,175, and 6,482,616; U.S. Patent Application Publications 2001/0043922 A1, 2002/0004040 A1, 2002/0031831 A1, 2002/0110545 A1, and 2004/0161848 A1; and International Patent Application Publications WO 94/28152, WO 95/02697, WO 95/16772, WO 95/34671, WO 96/22378, WO 97/12986, WO 97/21826, and WO 03/022311.

By removing all or part of, for example, the E1, E3, and/or E4 regions of the adenoviral genome, the resulting adenoviral vector is able to accept inserts of exogenous nucleic acid sequences while retaining the ability to be packaged into adenoviral capsids. The nucleic acid sequence can be positioned in the E1 region, the E3 region, or the E4 region of the adenoviral genome. Indeed, the nucleic acid sequence can be inserted anywhere in the adenoviral genome so long as the position does not prevent expression of the nucleic acid sequence or interfere with packaging of the adenoviral vector.

Replication-deficient adenoviral vectors are typically produced in complementing cell lines that provide gene functions not present in the replication-deficient adenoviral vectors, but required for viral propagation, at appropriate levels in order to generate high titers of viral vector stock. Desirably, the complementing cell line comprises, integrated into the cellular genome, adenoviral nucleic acid sequences which encode gene functions required for adenoviral propagation. A preferred cell line complements for at least one and preferably all replication-essential gene functions not present in a replication-deficient adenovirus. The complementing cell line can complement for a deficiency in at least one replication-essential gene function encoded by the early regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E4 region of the adenoviral genome.

Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially vaccination purposes. The lack of RCA in the vector stock avoids the replication of the adenoviral vector in non-complementing cells. Construction of such a complementing cell lines involve standard molecular biology and cell culture techniques, such as those described by Sambrook et al., supra, and Ausubel et al., supra.

Complementing cell lines for producing the adenoviral vector include, but are not limited to, 293 cells (described in, e.g., Graham et al., *J. Gen. Virol.*, 36, 59-72 (1977)), PER.C6 cells (described in, e.g., International Patent Application Publication WO 97/00326, and U.S. Pat. Nos. 5,994,128 and 6,033,908), and 293-ORF6 cells (described in, e.g., International Patent Application Publication WO 95/34671 and Brough et al., *J. Virol.*, 71: 9206-9213 (1997)). Additional complementing cells are described in, for example, U.S. Pat. Nos. 6,677,156 and 6,682,929, and International Patent Application Publication WO 03/20879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the desired adenoviral vector. Helper virus is often engineered to prevent packaging of infectious helper virus. For example, one or more replication-essential gene functions of the E1 region of the adenoviral genome are provided by the complementing cell, while one or more replication-essential gene functions of the E4 region of the adenoviral genome are provided by a helper virus.

The coat protein of an adenoviral vector can be manipulated to alter the binding specificity or recognition of a virus for a viral receptor on a potential host cell. For adenovirus, such manipulations can include deletion of regions of the fiber, penton, or hexon, insertions of various native or non-native ligands into portions of the coat protein, and the like. Manipulation of the coat protein can broaden the range of cells infected by the adenoviral vector or enable targeting of the adenoviral vector to a specific cell type.

Any suitable technique for altering native binding to a host cell, such as native binding of the fiber protein to the coxsackievirus and adenovirus receptor (CAR) of a cell, can be employed. For example, differing fiber lengths can be exploited to ablate native binding to cells. This optionally can be accomplished via the addition of a binding sequence to the penton base or fiber knob. This addition of a binding sequence can be done either directly or indirectly via a bispecific or multispecific binding sequence. In an alternative embodiment, the adenoviral fiber protein can be modified to reduce the number of amino acids in the fiber shaft, thereby creating a "short-shafted" fiber (as described in, for example, U.S. Pat. No. 5,962,311). Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a normative amino acid sequence either into the penton base or the fiber knob.

In yet another embodiment, the nucleic acid residues encoding amino acid residues associated with native substrate binding can be changed, supplemented, or deleted (see, e.g., International Patent Application Publication WO 00/15823, Einfeld et al., *J. Virol.*, 75(23): 11284-11291 (2001), and van Beusechem et al., *J. Virol.*, 76(6): 2753-2762 (2002)) such that the adenoviral vector incorporating the mutated nucleic acid residues (or having the fiber protein encoded thereby) is less able to bind its native substrate. In this respect, the native CAR and integrin binding sites of the adenoviral vector, such as the knob domain of the adenoviral fiber protein and an Arg-Gly-Asp (RGD) sequence located in the adenoviral penton base, respectively, can be removed or disrupted. Any suitable amino acid residue(s) of a fiber protein that mediates or assists in the interaction between the knob and CAR can be mutated or removed, so long as the fiber protein is able to trimerize. Similarly, amino acids can be added to the fiber knob as long as the fiber protein retains the ability to trimerize. Suitable residues include amino acids within the exposed loops of the serotype 5 fiber knob domain, such as, for example, the AB loop, the DE loop, the FG loop, and the HI loop, which are further described in, for example, Roelvink et al., *Science*, 286: 1568-1571 (1999), and U.S. Pat. No. 6,455,314. Any suitable amino acid residue(s) of a penton base protein that mediates or assists in the interaction between the penton base and integrins can be mutated or removed. Suitable residues include, for example, one or more of the five RGD amino acid sequence motifs located in the hypervariable region of the Ad5 penton base protein (as described, for example, in U.S. Pat. No. 5,731,190). The native integrin binding sites on the penton base protein also can be disrupted by modifying the nucleic acid sequence encoding the native RGD motif such that the native RGD amino acid sequence is conformationally inaccessible for binding to the αv integrin receptor, such as by inserting a DNA sequence into or adjacent to the nucleic acid sequence encoding the adenoviral penton base protein. Preferably, the adenoviral vector comprises a fiber protein and a penton base protein that do not bind to CAR and integrins, respectively. Alternatively, the adenoviral vector comprises fiber protein and a penton base protein that bind to CAR and integrins, respectively, but with less affinity than the corresponding wild type coat proteins. The adenoviral vector exhibits reduced binding to CAR and integrins if a modified adenoviral fiber protein and penton base protein binds CAR and integrins, respectively, with at least about 5-fold, 10-fold, 20-fold, 30-fold, 50-fold, or 100-fold less affinity than a non-modified adenoviral fiber protein and penton base protein of the same serotype.

The adenoviral vector also can comprise a chimeric coat protein comprising a non-native amino acid sequence that binds a substrate (i.e., a ligand), such as a cellular receptor other than CAR and the αv integrin receptor. The non-native amino acid sequence of the chimeric adenoviral coat protein allows an adenoviral vector comprising the chimeric coat protein to bind and, desirably, infect host cells not naturally infected by a corresponding adenovirus without the non-native amino acid sequence (i.e., host cells not infected by the corresponding wild-type adenovirus), and/or to bind to host cells naturally infected by the corresponding adenovirus with greater affinity than the corresponding adenovirus without the non-native amino acid sequence, or to bind to particular target cells with greater affinity than non-target cells. A "non-native" amino acid sequence can comprise an amino acid sequence not naturally present in the adenoviral coat protein or an amino acid sequence found in the adenoviral coat but located in a non-native position within the capsid.

Desirably, the adenoviral vector comprises a chimeric coat protein comprising a non-native amino acid sequence that confers to the chimeric coat protein the ability to bind to an immune cell more efficiently than a wild-type adenoviral coat protein. In particular, the adenoviral vector can comprise a chimeric adenoviral fiber protein comprising a non-native amino acid sequence which facilitates uptake of the adenoviral vector by immune cells, preferably antigen presenting cells, such as dendritic cells, monocytes, and macrophages. In a preferred embodiment, the adenoviral vector comprises a chimeric fiber protein comprising an amino acid sequence (e.g., a non-native amino acid sequence) comprising an RGD motif including, but not limited to, CRGDC (SEQ ID NO: 1), CXCRGDCXC (SEQ ID NO: 2), wherein X represents any amino acid, and CDCRGDCFC (SEQ ID NO: 3), which increases transduction efficiency of an adenoviral vector into dendritic cells. The RGD-motif, or any non-native amino acid sequence, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence. The spacer sequence preferably comprises between 1 and 200 amino acids, and can (but need not) have an intended function.

Where dendritic cells are the desired target cell, the non-native amino acid sequence can optionally recognize a protein typically found on dendritic cell surfaces such as adhesion proteins, chemokine receptors, complement receptors, co-stimulation proteins, cytokine receptors, high level antigen presenting molecules, homing proteins, marker proteins, receptors for antigen uptake, signaling proteins, virus receptors, etc. Examples of such potential ligand-binding sites in dendritic cells include αvβ3 integrins, αvβ5 integrins, 2A1, 7-TM receptors, CD1, CD11a, CD11b, CD11c, CD21, CD24, CD32, CD4, CD40, CD44 variants, CD46, CD49d, CD50, CD54, CD58, CD64, ASGPR, CD80, CD83, CD86, E-cadherin, integrins, M342, MHC-I, MHC-II, MIDC-8, MMR, OX62, p200-MR6, p55, S100, TNF-R, etc. Where dendritic cells are targeted, the ligand preferably recognizes the CD40 cell surface protein, such as, for example, by way of a CD-40 (bi)specific antibody fragment or by way of a domain derived from the CD40L polypeptide.

Where macrophages are the desired target, the non-native amino acid sequence optionally can recognize a protein typically found on macrophage cell surfaces, such as phosphatidylserine receptors, vitronectin receptors, integrins, adhesion receptors, receptors involved in signal transduction and/or inflammation, markers, receptors for induction of cytokines, or receptors up-regulated upon challenge by pathogens, members of the group B scavenger receptor cysteine-rich (SRCR) superfamily, sialic acid binding receptors, members of the Fc receptor family, B7-1 and B7-2 surface molecules, lymphocyte receptors, leukocyte receptors, antigen presenting molecules, and the like. Examples of suitable macrophage surface target proteins include, but are not limited to, heparin sulfate proteoglycans, αvβ3 integrins, αvβ5 integrins, B7-1, B7-2, CD11c, CD13, CD16, CD163, CD1a, CD22, CD23, CD29, Cd32, CD33, CD36, CD44, CD45, CD49e, CD52, CD53, CD54, CD71, CD87, CD9, CD98, Ig receptors, Fc receptor proteins (e.g., subtypes of Fcα, Fcγ, Fcε, etc.), folate receptor b, HLA Class I, Sialoadhesin, siglec-5, and the toll-like receptor-2 (TLR2).

Where B-cells are the desired target, the non-native amino acid sequence can recognize a protein typically found on B-cell surfaces, such as integrins and other adhesion molecules, complement receptors, interleukin receptors, phagocyte receptors, immunoglobulin receptors, activation markers, transferrin receptors, members of the scavenger receptor cysteine-rich (SRCR) superfamily, growth factor receptors, selectins, MHC molecules, TNF-receptors, and TNF-R associated factors. Examples of typical B-cell surface proteins include β-glycan, B cell antigen receptor (BAC), B7-2, B-cell receptor (BCR), C3d receptor, CD1, CD18, CD19, CD20, CD21, CD22, CD23, CD35, CD40, CD5, CD6, CD69, CD69, CD71, CD79a/CD79b dimer, CD95, endoglin, Fas antigen, human Ig receptors, Fc receptor proteins (e.g., subtypes of Fca, Fcg, Fcε, etc.), IgM, gp200-MR6, Growth Hormone Receptor (GH-R), ICAM-1, ILT2, CD85, MHC class I and II molecules, transforming growth factor receptor (TGF-R), α4β7 integrin, and αvβ3 integrin.

In another embodiment, the adenoviral vector can comprise a chimeric virus coat protein that is not selective for a specific type of eukaryotic cell. The chimeric coat protein differs from a wild-type coat protein by an insertion of a non-native amino acid sequence into or in place of an internal coat protein sequence, or attachment of a non-native amino acid sequence to the N- or C-terminus of the coat protein. For example, a ligand comprising about five to about nine lysine residues (preferably seven lysine residues) is attached to the C-terminus of the adenoviral fiber protein via a non-functional spacer sequence. In this embodiment, the chimeric virus coat protein efficiently binds to a broader range of eukaryotic cells than a wild-type virus coat, such as described in U.S. Pat. No. 6,465,253 and International Patent Application Publication WO 97/20051. Such an adenoviral vector can ensure widespread production of the antigen.

The ability of an adenoviral vector to recognize a potential host cell can be modulated without genetic manipulation of the coat protein, e.g., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type. Likewise, an antigen can be conjugated to the surface of the adenoviral particle through non-genetic means.

A non-native amino acid sequence can be conjugated to any of the adenoviral coat proteins to form a chimeric adenoviral coat protein. Therefore, for example, a non-native amino acid sequence can be conjugated to, inserted into, or attached to a fiber protein, a penton base protein, a hexon protein, protein IX, VI, or IIIa, etc. The sequences of such proteins, and methods for employing them in recombinant proteins, are well known in the art (see, e.g., U.S. Pat. Nos. 5,543,328; 5,559,099; 5,712,136; 5,731,190; 5,756,086; 5,770,442; 5,846,782; 5,962,311; 5,965,541; 5,846,782; 6,057,155; 6,127,525; 6,153,435; 6,329,190; 6,455,314; 6,465,253; 6,576,456; 6,649,407; 6,740,525, and International Patent Application Publications WO 96/07734, WO 96/26281, WO 97/20051, WO 98/07877, WO 98/07865, WO 98/40509, WO 98/54346, WO 00/15823, WO 01/58940, and WO 01/92549). The chimeric adenoviral coat protein can be generated using standard recombinant DNA techniques known in the art. Preferably, the nucleic acid sequence encoding the chimeric adenoviral coat protein is located within the adenoviral genome and is operably linked to a promoter that regulates expression of the coat protein in a wild-type adenovirus. Alternatively, the nucleic acid sequence encoding the chimeric adenoviral coat protein is located within the adenoviral genome and is part of an expression cassette which comprises genetic elements required for efficient expression of the chimeric coat protein.

The coat protein portion of the chimeric adenovirus coat protein can be a full-length adenoviral coat protein to which the ligand domain is appended, or it can be truncated, e.g., internally or at the C- and/or N-terminus. However modified (including the presence of the non-native amino acid), the chimeric coat protein preferably is able to incorporate into an adenoviral capsid. Where the non-native amino acid sequence is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber. Preferably the non-native amino acid sequence is added to the virion protein, and is incorporated in such a manner as to be readily exposed to a substrate, cell surface-receptor, or immune cell (e.g., at the N- or C-terminus of the adenoviral protein, attached to a residue facing a substrate, positioned on a peptide spacer, etc.) to maximally expose the non-native amino acid sequence. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate, cell surface receptor, or immune cell. Where the non-native amino acid sequence is attached to or replaces a portion of the hexon, preferably it is within a hypervariable region (Crawford-Miksza et al., *J. Virol.*, 70(3): 1836-44 (1996)). Where the non-native amino acid is attached to or replaces a portion of pIX, preferably it is within the C-terminus of pIX. Use of a spacer sequence to extend the non-native amino acid sequence away from the surface of the adenoviral particle can be advantageous in that the non-native amino acid sequence can be more available for binding to a receptor, and any steric interactions between the non-native amino acid sequence and the adenoviral fiber monomers can be reduced.

Binding affinity of a non-native amino acid sequence to a cellular receptor can be determined by any suitable assay, a variety of which assays are known and are useful in selecting a non-native amino acid sequence for incorporating into an adenoviral coat protein. Desirably, the transduction levels of host cells are utilized in determining relative binding efficiency. Thus, for example, host cells displaying $\alpha v\beta 3$ integrin on the cell surface (e.g., MDAMB435 cells) can be exposed to an adenoviral vector comprising the chimeric coat protein and the corresponding adenovirus without the non-native amino acid sequence, and then transduction efficiencies can be compared to determine relative binding affinity. Similarly, both host cells displaying $\alpha v\beta 3$ integrin on the cell surface (e.g., MDAMB435 cells) and host cells displaying predominantly $\alpha v\beta 1$ on the cell surface (e.g., 293 cells) can be exposed to the adenoviral vectors comprising the chimeric coat protein, and then transduction efficiencies can be compared to determine binding affinity.

In other embodiments (e.g., to facilitate purification or propagation within a specific engineered cell type), a non-native amino acid (e.g., ligand) can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol.*, 130: 1189 (1995)). A ligand can even bind non-peptide substrates, such as plastic (e.g., Adey et al., *Gene,* 156: 27 (1995)), biotin (Saggio et al., *Biochem. J.*, 293: 613 (1993)), a DNA sequence (Cheng et al., *Gene,* 171: 1 (1996), and Krook et al., *Biochem. Biophys., Res. Commun.*, 204: 849 (1994)), streptavidin (Geibel et al., *Biochemistry*, 34: 15430 (1995), and Katz, *Biochemistry*, 34: 15421 (1995)), nitrostreptavidin (Balass et al., *Anal. Biochem.*, 243: 264 (1996)), heparin (Wickham et al., *Nature Biotechnol.*, 14: 1570-73 (1996)), and other substrates.

Disruption of native binding of adenoviral coat proteins to a cell surface receptor can also render it less able to interact with the innate or acquired host immune system. Aside from pre-existing immunity, adenoviral vector administration induces inflammation and activates both innate and acquired immune mechanisms. Adenoviral vectors activate antigen-specific (e.g., T-cell dependent) immune responses, which limit the duration of transgene expression following an initial administration of the vector. In addition, exposure to adenoviral vectors stimulates production of neutralizing antibodies by B cells, which can preclude gene expression from subsequent doses of adenoviral vector (Wilson & Kay, *Nat. Med.*, 3(9): 887-889 (1995)). Indeed, the effectiveness of repeated administration of the vector can be severely limited by host immunity. In addition to stimulation of humoral immunity, cell-mediated immune functions are responsible for clearance of the virus from the body. Rapid clearance of the virus is attributed to innate immune mechanisms (see, e.g., Worgall et al., *Human Gene Therapy,* 8: 37-44 (1997)), and likely involves Kupffer cells found within the liver. Thus, by ablating native binding of an adenovirus fiber protein and penton base protein, immune system recognition of an adenoviral vector is diminished, thereby increasing vector tolerance by the host.

Another method for evading pre-existing host immunity to adenovirus, especially serotype 5 adenovirus, involves modifying an adenoviral coat protein such that it exhibits reduced recognition by the host immune system. Thus, the first and second adenoviral vectors of the inventive method preferably comprise such a modified coat protein. The modified coat protein preferably is a penton, fiber, or hexon protein. Most preferably, the modified coat protein is a hexon protein. The coat protein can be modified in any suitable manner, but is preferably modified by generating diversity in the coat protein. Preferably, such coat protein variants are not recognized by pre-existing host (e.g., human) adenovirus-specific neutralizing antibodies. Diversity can be generated using any suitable method known in the art, including, for example, directed evolution (i.e., polynucleotide shuffling) and error-prone PCR (see, e.g., Cadwell, *PCR Meth. Appl.,* 2: 28-33 (1991), Leung et al., *Technique,* 1:11-15 (1989), and Pritchard et al., *J. Theoretical Biol.*, 234: 497-509 (2005)). Preferably, coat protein diversity is generated through directed evolution techniques, such as those described in, e.g., Stemmer, *Nature,* 370: 389-91 (1994), Cherry et al., *Nat. Biotechnol.*, 17: 379-84 (1999), and Schmidt-Dannert et al., *Nat Biotechnol.*, 18(7): 750-53 (2000). In general, directed evolution involves three repeated operations: mutation, selection, and amplification. The primary steps performed in directed evolution typically include (1) mutation or recombination of a gene of interest, (2) construction of a library of the mutated or recombined genes, (3) expression of the library in suitable host cells, (4) selection of cells that express the variant with desired function or activity, and (5) isolation of a gene encoding a desired variant. This process is repeated until the desired number of variants is produced.

In the context of the invention, coat protein diversity is generated by first making random mutations in the gene encoding the coat protein by, for example, polynucleotide shuffling or error-prone PCR. The mutated coat protein genes are incorporated into a library of E1-deficient Ad5 adenoviral vectors, wherein each Ad5 vector comprises an Ad35 fiber protein and a dual expression cassette which expresses two marker genes (e.g., luciferase and green fluorescent protein) inserted into the E1 region. Library vectors are propagated in suitable host cells (e.g., *E. coli*), and vectors encoding potential coat protein variants of interest are rescued under competitive conditions in the presence of human anti-Ad5 neutralizing antibodies. Rescued vectors are either expanded in the presence of anti-Ad5 neutralizing antibodies, purified, or cloned, and coat protein variants are subjected to nucleic acid sequencing.

Once identified, the biological activity of the proteins encoded by the coat protein variants produced by the above strategy must be screened. Any suitable assay for measuring the desired biological activity of a coat protein variant can be used. For example, the importance of evaluating the growth properties of an Ad5 vector comprising a variant coat protein will be readily apparent to one of ordinary skill in the art. In addition, the immunogenicity of Ad5 vectors comprising a variant coat protein and encoding a heterologous antigen (e.g., a *Plasmodium* antigen) can be compared to a similar Ad5 vector comprising a wild-type coat protein. Moreover, because the ideal coat protein variant is not recognized by pre-existing adenovirus-specific neutralizing antibodies, it is necessary to evaluate the potential neutralizing effects of human serum on the coat protein variants.

Suitable modifications to an adenoviral vector are described in U.S. Pat. Nos. 5,543,328; 5,559,099; 5,712,136; 5,731,190; 5,756,086; 5,770,442; 5,846,782; 5,871,727; 5,885,808; 5,922,315; 5,962,311; 5,965,541; 6,057,155; 6,127,525; 6,153,435; 6,329,190; 6,455,314; 6,465,253; 6,576,456; 6,649,407; and 6,740,525; U.S. Patent Application Publications 2001/0047081 A1, 2002/0099024 A1, 2002/0151027 A1, 2003/0022355 A1, and 2003/0099619 A1, and International Patent Applications WO 96/07734, WO 96/26281, WO 97/20051, WO 98/07865, WO 98/07877, WO 98/40509, WO 98/54346, WO 00/15823, WO 01/58940, and WO 01/92549.

The invention utilizes a first and/or a second adenoviral vector, which may be the same or different. Each of the first and second adenoviral vectors comprises a heterologous nucleic acid sequence encoding a protein. A "heterologous nucleic acid sequence" is any nucleic acid sequence that is not obtained from, derived from, or based upon a naturally occurring nucleic acid sequence of the adenoviral vector. By "naturally occurring" is meant that the nucleic acid sequence can be found in nature and has not been synthetically modified. For example, the heterologous nucleic acid sequence can be a viral, bacterial, plant, or animal nucleic acid sequence. A sequence is "obtained" from a source when it is isolated from that source. A sequence is "derived" from a source when it is isolated from a source but modified in any suitable manner (e.g., by deletion, substitution (mutation), insertion, or other modification to the sequence) so as not to disrupt the normal function of the source gene. A sequence is "based upon" a source when the sequence is a sequence more than about 70% identical (preferably more than about 80% identical, more preferably more than about 90% identical, and most preferably more than about 95% identical) to the source but obtained through synthetic procedures (e.g., polynucleotide synthesis, directed evolution, etc.). Determining the degree of identity, including the possibility for gaps, can be accomplished using any suitable method (e.g., BLASTnr, provided by GenBank). Notwithstanding the foregoing, the heterologous nucleic acid sequence can be naturally found in the adenoviral vector, but located at a normative position within the adenoviral genome and/or operably linked to a normative promoter.

Any type of nucleic acid sequence (e.g., DNA, RNA, and cDNA) that can be inserted into an adenoviral vector can be used in connection with the invention. Each heterologous nucleic acid sequence encodes an antigen. An "antigen" is a molecule that induces an immune response in a mammal. An "immune response" can entail, for example, antibody production and/or the activation of immune effector cells (e.g., T cells). An antigen in the context of the invention can comprise any subunit, fragment, or epitope of any proteinaceous molecule, including a protein or peptide of viral, bacterial, parasitic, fungal, protozoan, prion, cellular, or extracellular origin, which ideally provokes an immune response in mammal, preferably leading to protective immunity. By "epitope" is meant a sequence on an antigen that is recognized by an antibody or an antigen receptor. Epitopes also are referred to in the art as "antigenic determinants."

The antigen is a parasite antigen such as, but not limited to, a parasite of the phylum Sporozoa (also referred to as phylum Apicomplexa) and genus *Plasmodium*. The antigen can be from any suitable *Plasmodium* species, but preferably is from a *Plasmodium* species that infects humans and causes malaria. Human-infecting *Plasmodium* species include *P. malariae, P. ovale, P. vivax,* and *P. falciparum. P. vivax* and *P. falciparum* are the most common, and *P. falciparum* is the most deadly, species of *Plasmodium* in human. In order to advance vaccine discovery, the genomes of a number of *Plasmodium* species have been sequenced. For example, the complete *P. falciparum* genome has been sequenced and is disclosed in Gardner et al., *Nature,* 419: 498-511 (2002). Thus, one of ordinary skill in the art can identify and isolate appropriate *Plasmodium* antigens using routine methods known in the art.

In nature, malaria parasites are spread by successively infecting two types of hosts: humans and female *Anopheles* mosquitoes. In this respect, malaria parasites are present as "sporozoites" in the salivary glands of the female *Anopheles* mosquito. When the *Anopheles* mosquito takes a blood meal on another human, the sporozoites are injected with the mosquito's saliva, enter the circulatory system, and within minutes of inoculation invade a human liver cell (hepatocyte). After invading hepatocytes, the parasite undergoes asexual replication. The stage of the parasite life cycle encompassing sporozoite and liver stages typically is referred to in the art as the "pre-erythrocytic stage," the "liver stage," or "the exo-erythrocytic stage." The progeny, called "merozoites," are released into the circulatory system following rupture of the host hepatocyte.

Merozoites released from the infected liver cells invade erythrocytes (red blood cells). The merozoites recognize specific proteins on the surface of the erythrocyte and actively invade the cell in a manner similar to other mosquito-borne parasites. After entering the erythrocyte, the parasite undergoes a trophic period followed by asexual replication to produce successive broods of merozoites. The progeny merozoite parasites grow inside the erythrocytes and destroy them, and then are released to initiate another round of infection. This stage of infection typically is referred to in the art as the "blood-stage" or "erythrocytic stage." Blood-stage parasites are those that cause the symptoms of malaria. When certain forms of blood-stage parasites (i.e., "gametocytes") are picked up by a female *Anopheles* mosquito during a blood meal, they start another, different cycle of growth and multiplication in the mosquito. The *Plasmodium* life cycle is described in, for example, Ramasamy et al., *Med. Vet. Entomol.*, 11(3): 290-6 (1997), Hall et al., *Science*, 307(5706): 82-6 (2005), and I. W. Sherman, ed., *Malaria: Parasite Biology, Pathogenesis, and Protection*, American Society of Microbiology (1998).

The *Plasmodium* antigen preferably is a *P. falciparum* antigen. Each of the first and second adenoviral vectors each comprises a heterologous nucleic acid sequence that can encodes a *P. falciparum* antigen that is expressed during the blood-stage of infection (a "blood-stage antigen") and/or that is expressed during the pre-erythrocytic stage of infection (a "pre-erythrocytic stage antigen"). Blood-stage antigens are known in the art to activate the humoral (i.e., antibody-mediated) arm of the immune system, while pre-erythrocytic stage antigens activate the cell-mediated arm of the immune system (i.e., T cell response). Suitable pre-erythrocytic stage antigens include, but are not limited to, circumsporozoite protein (CSP) and apical membrane antigen 1 (AMA-1). Preferably, the first adenoviral vector comprises a nucleic acid sequence encoding *P. falciparum* CSP, and the second adenoviral vector comprises a nucleic acid sequence encoding *P. falciparum* AMA-1 antigen. While it is preferred that the composition comprises a first and/or a second adenoviral vector, the composition can comprise a single adenoviral vector comprising a nucleic acid sequence encoding a *P. falciparum* CSP and a nucleic acid sequence encoding a *P. falciparum* AMA-1 antigen.

The *P. falciparum* antigen can be derived from any suitable *P. falciparum* strain. *P. falciparum* strains are known in the art and include, for example, the 3D7 strain, the IT strain, and the Ghanaian isolate. The complete genome of the *P. falciparum* 3D7 strain has been sequenced (see Gardiner et al., *Nature*, 419: 498-511 (2002)), and sequencing of the IT strain and the Ghanian isolate are in progress. Preferably, the first and second adenoviral vectors of the inventive method comprise heterologous nucleic acid sequences encoding antigens derived from the 3D7 strain of *P. falciparum*. One of ordinary skill in the art will appreciate, however, that the first and second adenoviral vectors can encode *P. falciparum* antigens derived from any strain, so long as the chosen antigen induces a sufficient immune response when expressed in a mammalian (e.g., human) host.

It will be appreciated that an entire, intact viral, bacterial, or parasitic protein is not required to produce an immune response. Indeed, most antigenic epitopes are relatively small in size, and, therefore, protein fragments can be sufficient for exposure to the immune system of the mammal. In addition, a fusion protein can be generated between two or more antigenic epitopes of one or more antigens. Delivery of fusion proteins via adenoviral vector to a mammal allows for exposure of an immune system to multiple antigens and, accordingly, enables a single vaccine composition to provide immunity against multiple pathogens. In addition, the heterologous nucleic acid sequence encoding a particular antigen can be modified to enhance the recognition of the antigen by the mammalian host. In this regard, the presence of a signal sequence and glycosylation may affect the immunogenicity of a *Plasmodium* antigen expressed by an adenoviral vector. While blood-stage antigens comprising a signal sequence have been shown to induce robust immune responses, a signal sequence is not always sufficient for the efficient secretion or trafficking of *P. falciparum* proteins (see, e.g., Yang et al., *Vaccine*, 15: 1303-13 (1997)). Similarly, glycosylation has been shown to reduce the efficacy of a vaccine candidate based on the C-terminal 42 kD fragment of the *P. falciparum* MSP-1 antigen (MSP1$_{42}$) (see, e.g., Stowers et al., *Proc. Natl. Acad. Sci. USA*, 99: 339-44 (2002)); however, results from studies investigating other *P. falciparum* DNA and protein vaccines demonstrate that glycosylation may not impact vaccine efficacy (see, e.g., Stowers et al, *Infect. Immun.*, 69: 1536-46 (2001)).

Thus the heterologous nucleic acid sequences described herein encode antigens that may or may not comprise a signal sequence. In one embodiment of the invention, the heterologous nucleic acid sequence present in the first and/or second adenoviral vector can encode a signal sequence. The term "signal sequence," as used herein, refers to an amino acid sequence, typically located at the amino terminus of a protein, which targets the protein to specific cellular compartments, such as the endoplasmic reticulum, and directs secretion of the mature protein from the cell in which it is produced. Signal sequences typically are removed from a precursor polypeptide and, thus, are not present in mature proteins. Any signal sequence that directs secretion of the protein encoded by the heterologous nucleic acid sequence is suitable for use in the invention. Preferably, the signal sequence is a heterologous signal sequence. More preferably, the signal sequence is from the human decay-accelerating factor (DAF) protein, which has been shown to enhance the cell-surface expression and secretion of *P. falciparum* MSP-1 protein (see, e.g., Burghaus et al., *Mol. Biochem. Parasitol.*, 104: 171-83 (1999)). The heterologous nucleic acid sequences in the adenoviral vectors of the inventive method desirably are constructed such that, when expressed, a signal sequence is located at the N-terminus of a protein encoded by a heterologous nucleic acid sequence. Alternatively, non-secreted (NS) versions of the antigens encoded by the heterologous nucleic acid sequences can be generated by any suitable means, but preferably are generated by deleting a signal sequence from the heterologous nucleic acid sequence. A nucleic acid sequence encoding *P. falciparum* AMA-1 antigen which lack a signal sequence include, for example, SEQ ID NO: 4 (AMA-1).

In addition, the heterologous nucleic acid sequences described herein encode antigens that may or may not be glycosylated (e.g., N-linked or O-linked glycosylation). Thus, the heterologous nucleic acid sequence present in the first and/or second adenoviral vector can encode an antigen that is not glycosylated (N-glycosylated or O-glycosylated). While recent studies indicate that *P. falciparum* proteins do not contain significant amounts of N-linked and O-linked carbohydrates (Gowda et al., *Parisitol. Today*, 15: 147-52 (1999)), some *P. falciparum* proteins contain potential glycosylation sites (Yang et al., *Glycobiology*, 9: 1347-56 (1999)). Glycosylation of the antigens encoded by the heterologous nucleic acid sequences in the adenoviral vectors of the inventive method can be inhibited by any suitable method. Preferably, glycosylation is inhibited by making mutations in glycosylation sites present in the heterologous nucleic acid sequences. Such mutations include those that would effect deletions, substitutions, and/or insertions of amino acids in the antigen. Preferably, glycosylation is inhibited by mutating a heterologous nucleic acid sequence encoding a *Plasmodium* antigen such that at least one amino acid of a glycosylation site is substituted with a different amino acid. For example, certain asparagines residues of the *P. falciparum* AMA-1 protein also can be substituted to inhibit glycosylation. For example, the asparagine residue at position 162 can be substituted with a lysine residue, and the asparagine residues at positions 266, 371, 421, 422, and 499 can be replaced with glutamine residues. These mutations are exemplary and in no way limiting. Indeed, any mutation can be utilized that disrupts a native glycosylation site. Nucleic acid sequences encoding *P. falciparum* AMA-1 comprising mutated glycosylation sites include, for example, SEQ ID NO: 6 and SEQ ID NO: 8.

The heterologous nucleic acid sequence desirably comprises codons expressed more frequently in humans than in the pathogen from which the heterologous nucleic acid sequence is derived. While the genetic code is generally universal across species, the choice among synonymous codons is often species-dependent. Infrequent usage of a particular codon by an organism likely reflects a low level of the corresponding transfer RNA (tRNA) in the organism. Thus, introduction of a nucleic acid sequence into an organism which comprises codons that are not frequently utilized in the organism may result in limited expression of the nucleic acid sequence. One of ordinary skill in the art would appreciate that, to achieve maximum protection against *Plasmodium* infection, the adenoviral vectors in the composition of the inventive method must be capable of expressing high levels of *Plasmodium* antigens in a mammalian, preferably a human, host. In this respect, the heterologous nucleic acid sequence preferably encodes the native amino acid sequence of a *Plasmodium* antigen, but comprises codons that are expressed more frequently in mammals (e.g., humans) than in *Plasmodium*. Such modified nucleic acid sequences are commonly described in the art as "humanized," as "codon-optimized," or as utilizing "mammalian-preferred" or "human-preferred" codons.

In the context of the invention, a *Plasmodium* nucleic acid sequence is said to be "codon-optimized" if at least about 60% (e.g., at least about 70%, at least about 80%, or at least about 90%) of the wild-type codons in the nucleic acid sequence are modified to encode mammalian-preferred codons. That is, a *Plasmodium* nucleic acid sequence is codon-optimized if at least about 60% of the codons encoded therein are mammalian-preferred codons. Preferred codon-optimized nucleic acid sequences encoding the *P. falciparum* CSP antigen include, for example, SEQ ID NO: 10, SEQ ID NO: 12, and SEQ ID NO: 14. A preferred codon-optimized nucleic acid sequence encoding the *P. falciparum* AMA-1 antigen comprises SEQ ID NO: 16. However, the invention is not limited to these exemplary sequences. Indeed, genetic sequences can vary between different strains, and this natural scope of allelic variation is included within the scope of the invention. Additionally and alternatively, the codon-optimized nucleic acid sequence encoding a *P. falciparum* antigen can be any sequence that hybridizes to above-described sequences under at least moderate, preferably high, stringency conditions, such as those described in Sambrook et al., supra. Determining the degree of homology can be accomplished using any suitable method (e.g., BLASTnr, provided by GenBank).

Each of the nucleic acid sequences in the first and second adenoviral vectors present in the composition of the invention desirably is present as part of an expression cassette, i.e., a particular nucleotide sequence that possesses functions which facilitate subcloning and recovery of a nucleic acid sequence (e.g., one or more restriction sites) or expression of a nucleic acid sequence (e.g., polyadenylation or splice sites). Each nucleic acid is preferably located in the E1 region (e.g., replaces the E1 region in whole or in part) or the E4 region of the adenoviral genome. For example, the E1 region can be replaced by one or more promoter-variable expression cassettes comprising a heterologous nucleic acid sequence. Alternatively, the E4 region can be replaced by one or more expression cassettes comprising a heterologous nucleic acid sequence. Inserting an expression cassette into the E4 region of the adenoviral genome inhibits formation of "revertant E1 adenovectors" (REA), because homologous recombination between the E1 region and the E1 DNA of a complementing cell line (e.g., 293 cell) or helper virus results in an E1-containing adenoviral genome that is too large for packaging inside an adenovirus capsid. Each expression cassette can be inserted in a 3'-5' orientation, e.g., oriented such that the direction of transcription of the expression cassette is opposite that of the surrounding adjacent adenoviral genome. However, it is also appropriate for an expression cassette to be inserted in a 5'-3' orientation with respect to the direction of transcription of the surrounding genome. In this regard, it is possible for the adenoviral vectors of the inventive method to comprise at least one nucleic acid sequence that is inserted into, for example, the E1 region in a 3'-5' orientation, and/or at least one nucleic acid sequence inserted into the E4 region in a 5'-3' orientation. The insertion of an expression cassette into the adenoviral genome (e.g., into the E1 region of the genome) can be facilitated by known methods, for example, by the introduction of a unique restriction site at a given position of the adenoviral genome. As set forth above, preferably all or part of the E3 region of the adenoviral vector also is deleted.

Preferably, each heterologous nucleic acid sequence is operably linked to (i.e., under the transcriptional control of) one or more promoter and/or enhancer elements, for example, as part of a promoter-variable expression cassette. Techniques for operably linking sequences together are well known in the art. Any promoter or enhancer sequence can be used in the context of the invention, so long as sufficient expression of the heterologous nucleic acid sequence is achieved and a robust immune response against the encoded antigen is generated. Preferably, the promoter is a heterologous promoter, in that the promoter is not obtained from, derived from, or based upon a naturally occurring promoter of the adenoviral vector. In this regard, the promoter can be a viral promoter. Suitable viral promoters include, for example, cytomegalovirus (CMV) promoters, such as the mouse CMV immediate-early promoter (mCMV) or the human CMV immediate-early promoter (hCMV) (described in, for example, U.S. Pat. Nos. 5,168,062 and 5,385,839), promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner et al., *Proc. Natl. Acad. Sci.*, 78: 144-145 (1981)), promoters derived from SV40 or Epstein Barr virus, an adeno-associated viral promoter, such as the p5 promoter, and the like. Preferably, the promoter is a human CMV immediate-early promoter.

Alternatively, the promoter can be a cellular promoter, i.e., a promoter that is native to eukaryotic, preferably animal, cells. In one aspect, the cellular promoter is preferably a constitutive promoter that works in a variety of cell types, such as cells associated with the immune system. Suitable constitutive promoters can drive expression of genes encoding transcription factors, housekeeping genes, or structural genes common to eukaryotic cells. Suitable cellular promoters include, for example, a ubiquitin promoter (e.g., a UbC promoter) (see, e.g., Marinovic et al., *J. Biol. Chem.*, 277(19): 16673-16681 (2002)), a human β-actin promoter, an EF-1α promoter, a YY1 promoter, a basic leucine zipper nuclear factor-1 (BLZF-1) promoter, a neuron specific enolase (NSE)

promoter, a heat shock protein 70B (HSP70B) promoter, and a JEM-1 promoter. Preferably, the cellular promoter is a ubiquitin promoter.

Many of the above-described promoters are constitutive promoters. Instead of being a constitutive promoter, the promoter can be an inducible promoter, i.e., a promoter that is up- and/or down-regulated in response to an appropriate signal. The use of a regulatable promoter or expression control sequence is particularly applicable to DNA vaccine development inasmuch as antigenic proteins, including viral and parasite antigens, frequently are toxic to complementing cell lines. A promoter can be up-regulated by a radiant energy source or by a substance that distresses cells. For example, an expression control sequence can be up-regulated by drugs, hormones, ultrasound, light activated compounds, radiofrequency, chemotherapy, and cyofreezing. Thus, the promoter sequence that regulates expression of the heterologous nucleic acid sequence can contain at least one heterologous regulatory sequence responsive to regulation by an exogenous agent. Suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed.

The promoter can be a tissue-specific promoter, i.e., a promoter that is preferentially activated in a given tissue and results in expression of a gene product in the tissue where activated. A tissue-specific promoter suitable for use in the invention can be chosen by the ordinarily skilled artisan based upon the target tissue or cell-type. Preferred tissue-specific promoters for use in the inventive method are specific to immune cells, such as the dendritic-cell specific Dectin-2 promoter described in Morita et al., *Gene Ther.*, 8: 1729-37 (2001).

In yet another embodiment, the promoter can be a chimeric promoter. A promoter is "chimeric" in that it comprises at least two nucleic acid sequence portions obtained from, derived from, or based upon at least two different sources (e.g., two different regions of an organism's genome, two different organisms, or an organism combined with a synthetic sequence). Preferably, the two different nucleic acid sequence portions exhibit less than about 40%, more preferably less than about 25%, and even more preferably less than about 10% nucleic acid sequence identity to one another (which can be determined by methods described elsewhere herein). Chimeric promoters can be generated using standard molecular biology techniques, such as those described in Sambrook et al., *Molecular Cloning, a Laboratory Manual*, $3^{rd}$ edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

A promoter can be selected for use in the method of the invention by matching its particular pattern of activity with the desired pattern and level of expression of the antigen(s). In this respect, the adenoviral vector preferably comprises two or more heterologous nucleic acid sequences that encode different antigens and are operably linked to different promoters displaying distinct expression profiles. For example, a first promoter is selected to mediate an initial peak of antigen production, thereby priming the immune system against an encoded antigen. A second promoter is selected to drive production of the same or different antigen such that expression peaks several days after the initial peak of antigen production driven by the first promoter, thereby "boosting" the immune system against the antigen. Alternatively, a chimeric promoter can be constructed which combines the desirable aspects of multiple promoters. For example, a CMV-RSV hybrid promoter combining the CMV promoter's initial rush of activity with the RSV promoter's high maintenance level of activity is especially preferred for use in many embodiments of the inventive method. In addition, a promoter can be modified to include heterologous elements that enhance its activity. For example, a human CMV promoter sequence can include a synthetic splice signal, which enhances expression of a nucleic acid sequence operably linked thereto. In that antigens can be toxic to eukaryotic cells, it may be advantageous to modify the promoter to decrease activity in complementing cell lines used to propagate the adenoviral vector.

To optimize protein production, preferably each heterologous nucleic acid sequence further comprises a polyadenylation site 3' of the coding sequence. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Simian Virus-40) polyadenylation sequence. Also, preferably all the proper transcription signals (and translation signals, where appropriate) are correctly arranged such that the nucleic acid sequence is properly expressed in the cells into which it is introduced. If desired, the heterologous nucleic acid sequence also can incorporate splice sites (i.e., splice acceptor and splice donor sites) to facilitate mRNA production.

In the method of the invention, the first adenoviral vector and/or the second adenoviral vector are/is administered to a mammal (e.g., a human), wherein the nucleic acid sequences encoding the *Plasmodium* antigens are expressed to produce the antigens in the mammal so as to induce an immune response against the antigens. The first and/or second adenoviral vectors typically will be administered in composition form. Thus, a composition comprising the first adenoviral vector or a composition comprising the second adenoviral vector can be administered to the mammal. Preferably, both a composition comprising the first adenoviral vector and a composition comprising the second adenoviral vector are administered to the mammal. While the first and second adenoviral vectors can be separately formulated and administered simultaneously or sequentially in any order, most preferably, the first and second adenoviral vectors are part of a single, i.e., the same, composition, which is administered to the mammal.

The immune response induced by the inventive method can be a humoral immune response, a cell-mediated immune response, or, desirably, a combination of humoral and cell-mediated immunity. Ideally, the immune response provides protection upon subsequent challenge with the infectious agent comprising the antigen. However, protective immunity is not required in the context of the invention. The inventive method further can be used for antibody production and harvesting.

Administering the composition(s) comprising the first and/or second adenoviral vectors encoding *Plasmodium* antigens can be one component of a multistep regimen for inducing an immune response in a mammal. In particular, the inventive method can represent one arm of a prime and boost immunization regimen. The inventive method, therefore, can comprise administering to the mammal the composition(s) as a priming composition(s) or as a boosting composition(s). When the composition(s) is(are) administered to boost an immune response, a priming composition is administered to the mammal prior to administration of the composition(s) comprising the first and/or second adenoviral vectors. When the composition(s) is(are) administered to prime an immune response, a boosting composition is administered to the mammal after administration of the composition comprising the first and/or second adenoviral vectors. In either case, the priming composition or the boosting composition(s) can comprise a gene transfer vector comprising a nucleic acid sequence encoding at least one antigen. The antigen encoded by the gene transfer vector can be the same or different from the antigens encoded by the first and/or second adenoviral vectors.

Any gene transfer vector can be employed in the priming composition or the boosting composition, including, but not limited to, a plasmid, a retrovirus, an adeno-associated virus, a vaccinia virus, a herpesvirus, an alphavirus, or an adenovirus. Ideally, the priming gene transfer vector is a plasmid, an alphavirus, or an adenoviral vector of any serotype. To maximize the effect of the priming regimen, the priming gene transfer vector can comprise more than one heterologous nucleic acid sequence (e.g., 2, 3, 5, or more) encoding an antigen. Alternatively, an immune response can be primed or boosted by administration of the antigen itself, e.g., an antigenic protein, intact pathogen (e.g., *Plasmodium* sporozoites), parasitized erythrocytes, inactivated pathogen, and the like. A boosting composition can be administered to the mammal in any suitable timeframe following administration of a priming composition. For example, the boosting composition can be administered to the mammal at least 5 days, about 1 week, 2 weeks, 4 weeks, 8 weeks, 12 weeks, 16 weeks, or more following priming to maintain immunity. Preferably, the time interval between administration of the priming and boosting compositions is at least 10 days, and not more than six months (e.g., at least 10 days, 2 weeks, 1 month, 2 months, 3 months, 4 months, or 5 months). One of ordinary skill in the art will appreciate that more than one priming composition and more than one boosting composition can be provided to achieve and maintain immunity against a particular pathogen.

In a preferred embodiment of the invention, the composition(s) comprising the first and/or second adenoviral vectors is administered to the mammal to prime an immune response, and then a boosting composition is administered to the mammal. The boosting composition comprises a *P. falciparum* circumsporozoite protein (CSP), or an immunogenic portion thereof, and/or a *P. falciparum* apical membrane antigen 1 (AMA-1) antigen, or an immunogenic portion thereof. An "immunogenic portion" of an antigen is a fragment of the antigen that is capable of eliciting an immune response in vivo. The immunogenic portion can be of any size, and is preferably at least three amino acids in length (e.g., at least 4, 5, or more amino acids), more preferably at least 7 amino acids in length (e.g., at least 8, 9, or more amino acids), and most preferably at least 10 amino acids in length (e.g., 10, 15, 20, or more amino acids). Preferably, the immunogenic portion comprises an epitope of the antigen. By "epitope" is meant a sequence on an antigen that is recognized by an antibody or an antigen receptor. Epitopes also are referred to in the art as "antigenic determinants."

In another embodiment, the composition(s) comprising the first and/or second adenoviral vectors is administered to the mammal to boost an immune response that has been primed by administering a different priming composition. The priming composition desirably comprises plasmid DNA or a viral vector encoding *P. falciparum* circumsporozoite protein (CSP), or an immunogenic portion thereof, and/or a *P. falciparum* apical membrane antigen 1 (AMA-1) antigen, or an immunogenic portion thereof. The viral vector can be any of those described herein, and preferably is an adenoviral vector of a different serotype than the first and/or second adenoviral vectors.

Any route of administration can be used to deliver the first and/or second adenoviral vectors to the mammal. Although more than one route can be used to administer the composition, a particular route can provide a more immediate and more effective reaction than another route. Preferably, the composition(s) comprising the first and/or second adenoviral vectors is(are) administered via intramuscular injection. The composition(s) also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The composition(s) can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the composition(s) comprising the first and/or second adenoviral vectors. The composition(s) also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of the first adenoviral vector and/or the second adenoviral vector administered to the mammal will depend on a number of factors, including the size of a target tissue, the extent of any side-effects, the particular route of administration, and the like. The dose ideally comprises an "effective amount" of adenoviral vector, i.e., a dose of adenoviral vector which provokes a desired immune response in the mammal. The desired immune response can entail production of antibodies, protection upon subsequent challenge, immune tolerance, immune cell activation, and the like. Desirably, a single dose of each of the first and second adenoviral vectors comprises at least about $1 \times 10^5$ particles (which also is referred to as particle units) of the adenoviral vector. The dose of each of the adenoviral vectors in the composition preferably is at least about $1 \times 10^6$ particles (e.g., about $1 \times 10^6$ to about $1 \times 10^{12}$ particles), at least about $1 \times 10^7$ particles, at least about $1 \times 10^8$ particles (e.g., about $1 \times 10^8$ to about $1 \times 10^{11}$ particles), more preferably at least about $1 \times 10^9$ particles (e.g., about $5 \times 10^9$ to about $5 \times 10^{10}$ particles), and more preferably at least about $1 \times 10^{10}$ particles (e.g., about $1 \times 10^{10}$ to about $1 \times 10^{11}$ particles) of the first and/or second adenoviral vectors. The dose of each of the first and/or second adenoviral vectors desirably comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles. In other words, a single dose of each of the first and second adenoviral vectors can comprise, for example, about $1 \times 10^6$ particle units (pu), $2 \times 10^6$ pu, $4 \times 10^6$ pu, $1 \times 10^7$ pu, $2 \times 10^7$ pu, $4 \times 10^7$ pu, $1 \times 10^8$ pu, $2 \times 10^8$ pu, $4 \times 10^8$ pu, $1 \times 10^9$ pu, $2 \times 10^9$ pu, $4 \times 10^9$ pu, $1 \times 10^{10}$ pu, $2 \times 10^{10}$ pu, $4 \times 10^{10}$ pu, $5 \times 10^{10}$ pu, $1 \times 10^{11}$ pu, $2 \times 10^{11}$ pu, $4 \times 10^{11}$ pu, $1 \times 10^{12}$ pu, $2 \times 10^{12}$ pu, or $4 \times 10^{12}$ pu of each of the adenoviral vectors.

The composition(s) comprising the first and/or second adenoviral vectors desirably is administered at least once to a mammal in need thereof. It will be appreciated, however, that immunity against a particular pathogen (e.g., *P. falciparum*) is often most effectively achieved by multiple immunizations with a particular vaccine composition. Thus, the composition(s) preferably is/are administered to a mammal more than once (e.g., 2, 3, 4, 5, or more times). When the composition is administered to a mammal multiple times, any suitable amount of time may pass between each administration. In this respect, the duration between each administration can be days (e.g., 1, 2, 3, 4, or 5 or more days), weeks (1, 2, or 3 or more weeks), or months (1, 2, or 3 or more months), as determined by a clinician.

The composition comprises the first and/or second adenoviral vectors described herein as well as a carrier, preferably a pharmaceutically (e.g., physiologically acceptable) carrier. Any suitable carrier can be used within the context of the invention, and such carriers are well known in the art. The choice of carrier will be determined, in part, by the particular site to which the composition is to be administered and the particular method used to administer the composition. Ideally, in the context of adenoviral vectors, the composition preferably is free of replication-competent adenovirus. The composition optionally can be sterile or sterile with the exception of the first and second adenoviral vectors.

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the composition is formulated to protect the adenoviral vectors from damage prior to administration. For example, the composition can be formulated to reduce loss of the adenoviral vectors on devices used to prepare, store, or administer the expression vector, such as glassware, syringes, or needles. The composition can be formulated to decrease the light sensitivity and/or temperature sensitivity of the adenoviral vectors. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenoviral vectors, facilitate administration, and increase the efficiency of the inventive method. Formulations for adenoviral vector-containing compositions are further described in, for example, U.S. Pat. No. 6,225,289, U.S. Pat. No. 6,514,943, U.S. Patent Application Publication 2003/0153065 A1, and International Patent Application Publication WO 00/34444. A composition also can be formulated to enhance transduction efficiency. In addition, one of ordinary skill in the art will appreciate that the first and/or second adenoviral vectors can be present in a composition with other therapeutic or biologically-active agents. For example, factors that control inflammation, such as ibuprofen or steroids, can be part of the composition to reduce swelling and inflammation associated with in vivo administration of the viral vector. As discussed herein, immune system stimulators or adjuvants, e.g., interleukins, lipopolysaccharide, and double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

The following examples further illustrate the invention but, of course, should not be construed as in any way limiting its scope.

Example 1

This example demonstrates the preparation and immunogenicity of a composition comprising a first adenoviral vector encoding *P. falciparum* CSP and a second adenoviral vector encoding *P. falciparum* AMA-1 antigen.

Two serotype 5 E1/E3/E4-deficient adenoviral vectors containing, in place of the deleted E1 region, a nucleic acid sequence encoding a codon-optimized *P. falciparum* CSP (NMRC-M3V-Ad-PjC) and a codon-optimized *P. falciparum* AMA-1 (NMRC-M3V-Ad-PfA) antigen, respectively, were generated using the methods described in, for example, International Patent Application Publication No. WO 99/15686 and U.S. Pat. No. 6,329,200. In each adenoviral vector construct, the CSP gene (SEQ ID NO: 10) and the AMA-1 gene (SEQ ID NO: 16) were expressed from an expression cassette inserted into the site of the E1 deletion in the opposite orientation with respect to adenoviral vector transcription. The expression cassette contains, from 5' to 3', the human CMV promoter (hCMV) having a synthetic splice signal, the CSP gene or the AMA-1 gene, and an SV40 polyadenylation signal.

BALB/c mice (6 per group) were immunized intramuscularly at days 1 and 14 with $1 \times 10^8$ pu NMRC-M3V-Ad-PfC ($1 \times 10^{11}$ pu/ml stock) or NMRC-M3V-Ad-PfA ($1 \times 10^{11}$ pu/ml stock) in a total volume of 100 μl split between the tibialis anterior muscles, either separately or cocktailed (NMRC-M3V-Ad-PfCA) as indicated in Table 1.

A parallel group of mice was immunized with a negative control adenoviral vector (AdNull). Sera was collected pre-immunization, at 10 days after each immunization, and at study termination (day 28) for evaluation of vaccine-induced antibody responses. Splenocytes were harvested at day 28 for evaluation of vaccine-induced T cell responses. Statistical significance of outcome measures was evaluated using the 2-sided chi-square test (STATA version 6.0, STATA Corp, 1999).

TABLE 1

| Group | Test Vector | Day of Dosing | Day of Study End | Dose (pu) | Route |
|---|---|---|---|---|---|
| 1 | Adnull | 1 and 14 | 28 | $1 \times 10^8$ | IM |
| 2 | NMRC-M3VAd-PfC | 1 and 14 | 28 | $1 \times 10^8$ | IM |
| 3 | NMRC-M3VAd-PfA | 1 and 14 | 28 | $1 \times 10^8$ | IM |
| 4 | NMRC-M3V-Ad-PfCA | 1 and 14 | 28 | $1 \times 10^8$ (each vector) | IM |
| 5 | NMRC-M3VAd-PfC + NMRC-M3VAd-PfA (separate sites) | 1 and 14 | 28 | $1 \times 10^8$ (each vector) | IM |

Antigen-specific antibodies were assessed by ELISA using recombinant CSP protein or recombinant AMA-1 protein as capture antigens (*P. falciparum* 3D7 strain). The recombinant CSP protein was produced in *E. coli*, and the recombinant AMA-1 protein was produced in *Pichia pastoris*. Both recombinants were manufactured at the Walter Reed Army Institute of Research Pilot Bioproduction Facility (Silver Spring, Md.). Mouse sera specific for both PfCSP and PfAMA1 antigens were generated, quality controlled, and used as reference standards for all ELISA assays. Two-fold dilutions of reference sera were plated in quadruplicate to generate a standard curve (4-parameter fit). Standard curve parameters were applied to OD values (405 nm-490 nm) of test samples to calculate unit values. Test samples were assayed at dilutions of 1/500 and 1/5000. NMRC-M3V-Ad-PfCA, NMRC-M3V-Ad-PfC, and NMRC-M3V-Ad-PfA were immunogenic in treated mice, as evidenced by the presence of PfCSP- and PfAMA-1-specific antibodies detected by the ELISA assay.

Antigen-specific T cell responses were assessed by ex vivo IFN-γ ELIspot using MHC-matched A20.2J (ATCC clone HB-98) transiently transfected with either PfCSP plasmid DNA or PfAMA-1 plasmid DNA using the Amaxa nucleofector system (Amaxa Inc., Gaithersburg, Md.) according to manufacturer's instructions. Responses also were evaluated against synthetic peptides representing a defined CD8+ T cell epitope from PfCSP (residues 39-47) or a pool of synthetic peptides (15-mers) spanning the entire PfCSP. Quadruplicate wells were tested in all assays. VR1020 transfected or unpulsed target cells served as controls for DNA-transfected or peptide pulsed targets, respectively. The number of IFN-γ secreting cells, visualized as spots, was determined using an automated ELIspot Reader (Zeiss K S, Zeiss Inc., Germany). NMRC-M3V-Ad-PfCA, NMRC-M3V-Ad-PfC, and NMRC-M3V-Ad-PfA were immunogenic in treated mice, as evidenced by the presence of IFN-γ secreting cells, as compared to AdNull-treated mice or naïve mice.

There was no significant difference in either antibody responses or T cell responses elicited at any timepoint when NMRC-M3V-Ad-PfC VDP and NMRC-M3V-Ad-PfA VDP were administered in separate sites or as a cocktail in the same site (p>0.10). There was no significant difference in antibody responses or T cell responses to antigen-transfected targets elicited at any timepoint when NMRC-M3V-Ad-PfC VDP or NMRC-M3V-Ad-PfA VDP were administered individually, or in combination, at either the same site or at separate sites (p>0.10).

The results of this example demonstrate that a composition comprising a PfCSP-encoding adenoviral vector and a PfAMA-1-encoding adenoviral vector is immunogenic in mammals.

Example 2

This example demonstrates the safety and immunogenicity of a composition comprising a first adenoviral vector encoding P. falciparum CSP and a second adenoviral vector encoding P. falciparum AMA-1 in vivo.

The immunogenicity of NMRC-M3V-Ad-PfC, NMRC-M3V-Ad-PfA, and NMRC-M3V-Ad-PfCA described in Example 1 was investigated in New Zealand White (NZW) rabbits. Specifically, four groups of five rabbits each were administered with either PBS (control), adenovector final formulation buffer (FFB) (control), NMRC-M3V-Ad-PfCA ($2\times10^{10}$ pu), or NMRC-M3V-Ad-PfCA ($1\times10^{11}$ pu) on days 1, 11, and 32 of the study period. A fifth group of rabbits received PBS on study days 1, 15, and 29, and FFB on study day 43 and 53. A sixth group received a priming immunization consisting of a plasmid encoding PfCSP and a plasmid encoding PfAMA1 (NMRC-M3V-D-PfCA) (1.0 mg) on study days 1, 15, and 29, and a boosting immunization with NMRC-M3V-Ad-PfCA ($1\times10^{11}$ pu) on study days 43 and 53. Following necropsy, the following toxicology screens were evaluated: clinical observations, mortality, gross pathology, organ weights and ratios, ophthalmology, clinical chemistry, hematology, coagulation, histopathology, and immunology.

With regard to mortality, all treated animals survived to scheduled end dates. In addition, treatment with NMRC-M3V-Ad-PfCA had no effect on mortality. Treatment with NMRC-M3V-Ad-PfCA also produced no adverse effects at the injection sites. In this respect, minimal erythema and edema were noted in all groups following dosing and usually resolved within 2-5 days. No increase in erythema and edema severity with repeated dosing was observed. There was no apparent difference between sexes. Minimal to mild host inflammatory responses in the skeletal muscle at the injection site were observed, and there was no increased severity with repeat dosing. Treatment with NMRC-M3V-Ad-PfCA was generally well tolerated, as evidenced by the absence of any effects on food consumption, body weight, organ weight, and ophthalmology.

In groups 1-4, immunology was assessed at the study start, two days after administration of the composition, and at necroscopy using PfCSP- and PfAMA1-specific ELISA. Administration of NMRC-M3V-Ad-PfCA produced PfCSP- and PfAMA-1 specific antibody responses.

The results of this example demonstrate that a composition comprising a PfCSP-encoding adenoviral vector and a PfAMA1-encoding adenoviral vector is well-tolerated and immunogenic in mammals.

Example 3

This example demonstrates a method of administering a composition comprising a first adenoviral vector encoding P. falciparum CSP and a second adenoviral vector encoding P. falciparum AMA-1 to humans in vivo.

A Phase 1/2a randomized, open-label clinical trial assessing the safety, tolerability, immunogenicity, and protective efficacy of the vaccine construct NMRC-M3V-Ad-PfCA (described in Example 1) will be conducted in two parts. The first part (Part A) is a dose escalation study of NMRC-M3V-Ad-PfCA in 12 human volunteers. Specifically, two dose groups ($2\times10^{10}$ pu and $1\times10^{11}$ pu) of six volunteers each will receive a single intramuscular (IM) injection of NMRC-M3V-Ad-PfCA. Administration of NMRC-M3V-Ad-PfCA in the two groups will be staggered by four weeks so as to assess the safety and tolerability of the vaccine and define the dose to be used in the second part (Part B) of the clinical study, which is anticipated to be $1\times10^{11}$ pu. The specific dosing regimens of Parts A and B of the clinical trial are set forth in Table 2.

Following completion of Part A, Part B of the two-part trial will commence. Part B will compare the effects of administration of NMRC-M3V-Ad-PfCA at two dosing intervals to the effects of administration of the individual adenoviral vector components of NMRC-M3V-Ad-PfCA (i.e., NMRC-M3V-Ad-PfC and NMRC-M3V-Ad-PCA). Five groups of ten volunteers each and eight infectivity controls will receive one or two IM injections of NMRC-M3V-Ad-PfCA, NMRC-M3V-Ad-PfC, or NMRC-M3V-Ad-PCA as set forth in Table 2.

TABLE 2

Part A

| Group | Test Article | Volunteers per Group | Week 0 | Week 4 | Weeks 8-12 |
|---|---|---|---|---|---|
| 1 | NMRC-M3V-Ad-PfCA | 6 | $2 \times 10^{10}$ pu | none | Review of safety data |
| 2 | NMRC-M3V-Ad-PfCA | 6 | none | $1 \times 10^{11}$ pu | |

Part B

| | Test Article | Volunteers per Group | Week 16 | Week 30.5 | Week 32 | Week 35 | Weeks 36-37 | Weeks 38-41 |
|---|---|---|---|---|---|---|---|---|
| 3 | NMRC-M3V-Ad-PfCA | 10 | $1 \times 10^{11}$ pu | | $1 \times 10^{11}$ pu | sporozoite challenge | Twice daily smears, overnight stays | Final clinical visit/begin follow-up |
| 4 | NMRC-M3V-Ad-PfCA | 10 | | $1 \times 10^{11}$ pu | $1 \times 10^{11}$ pu | sporozoite challenge | Twice daily smears, overnight stays | Final clinical visit/begin follow-up |
| 5 | NMRC-M3V-Ad-PfCA | 10 | | | $1 \times 10^{11}$ pu | sporozoite challenge | Twice daily smears, overnight stays | Final clinical visit/begin follow-up |
| 6 | NMRC-M3V-Ad-PfC | 10 | | | $5 \times 10^{10}$ pu | sporozoite challenge | Twice daily smears, overnight stays | Final clinical visit/begin follow-up |
| 7 | NMRC-M3V-Ad-PfA | 10 | | | $5 \times 10^{10}$ pu | sporozoite challenge | Twice daily smears, overnight stays | Final clinical visit/begin follow-up |
| 8 | None (infectivity controls) | 8 | | | | sporozoite challenge | Twice daily smears, overnight stays | Final clinical visit |

For Part B, each treatment group will be split into two cohorts of five subjects each. One set of cohorts from each group (groups 3-7) will be immunized and challenged with *P. falciparum* sporozoites at a three-week stagger from the other set of cohorts. The infectivity control group will be split into cohorts in the same manner. Sporozoite challenge will be conducted three weeks after the last immunization using five infectious mosquito bites in order to assess protective immunity and allow for evaluation of surrogate markers of protection.

For Part A, primary endpoints include assessment of the safety and tolerability of NMRC-M3V-Ad-PfCA in healthy, malaria naïve adults. Secondary endpoints include assessment of the immunogenicity of NMRC-M3V-Ad-PfCA. To this end, anti-CSP immune responses will be assessed using an IFN-γ ELIspot assay against synthetic peptides derived from PfCSP using peripheral blood mononuclear cells (PBMCs) collected pre-immunization, and at 10 and 28 days post-immunization. Anti-AMA1 immune responses will be assessed using an ELISA assay of sera/plasma collected pre-immunization, and at 10 and 28 days post-immunization.

For Part B, primary endpoints include assessment of the safety and tolerability of NMRC-M3V-Ad-PfCA, NMRC-M3V-Ad-PfC, and NMRC-M3V-Ad-PfA in volunteers, and assessment of the protective efficacy against sporozoite challenge provided by NMRC-M3V-Ad-PfCA, NMRC-M3V-Ad-PfC, and NMRC-M3V-Ad-PfA. Secondary endpoints include (1) assessment of the immunogenicity of NMRC-M3V-Ad-PfCA, NMRC-M3V-Ad-PfC, and NMRC-M3V-Ad-PfA, (2) comparison of the immunogenicity and protective efficacy of one versus two doses of NMRC-M3V-Ad-PfCA, and (3) comparison of the immunogenicity and protective efficacy of two doses of NMRC-M3V-Ad-PfCA administered at short (10 days) versus long (16 weeks) intervals. To this end, anti-CSP immune responses will be assessed using an IFN-γ ELIspot assay against synthetic peptides derived from PfCSP using peripheral blood mononuclear cells (PBMCs) collected pre-immunization, 10 days post-immunization, day of challenge, and 28 days post-immunization. Anti-AMA1 immune responses will be assessed using an ELISA assay of sera/plasma collected pre-immunization, 10 days post-immunization, day of challenge, and 28 days post-immunization.

If, as expected, NMRC-M3V-Ad-PfCA administration affords protection against experimental sporozoite challenge, the inventive method will undergo further Phase 1a and Phase 2a testing in the United States, followed by Phase 1b and Phase 2b testing in malaria-endemic countries.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inducing an immune response against malaria in a mammal, which method comprises:
    (a) administering a priming composition to the mammal, wherein the priming composition comprises a plasmid encoding a P. falciparum circumsporozoite protein (CSP), or an immunogenic portion thereof, and/or a P. falciparum apical membrane antigen 1 (AMA-1) antigen, or an immunogenic portion thereof; and
    (b) intramuscularly administering to a mammal a composition comprising a pharmaceutically acceptable carrier and either or both of:
    (1) about $1\times10^6$ particle units (pu) to about $1\times10^{12}$ pu of a first adenoviral vector comprising an adenoviral genome comprising a left inverted terminal repeat (ITR), the E2A region, the E2B region, late regions LI-LS, and a right ITR, and a nucleic acid sequence encoding a P. falciparum circumsporozoite protein (CSP) operably linked to a human CMV promoter, and
    (2) about $1\times10^6$ particle units pu to about $1\times10^{12}$ pu of a second adenoviral vector comprising an adenoviral genome comprising a left inverted terminal repeat (ITR), the E2A region, the E2B region, late regions LI-LS, and a right ITR, and a nucleic acid sequence encoding a P. falciparum apical membrane antigen 1 (AMA-1) antigen operably linked to a human CMV promoter, wherein the composition is administered to the mammal one or more times, and wherein the nucleic acid sequence encoding a P. falciparum CSP and/or the nucleic acid sequence encoding a P. falciparum AMA-1 are expressed to produce the CSP and/or the AMA-1 in the mammal to induce an immune response against malaria.

2. The method of claim 1, wherein the composition comprises the first adenoviral vector and the second adenoviral vector.

3. The method of claim 2, wherein the composition comprises About $5\times10^9$ pu to about $5\times10^{10}$ pu of the first adenoviral vector and about $5\times10^9$ pu to about $5\times10^{10}$ pu of the second adenoviral vector.

4. The method of claim 3, wherein the composition comprises about $1\times10^{10}$ pu of the first adenoviral vector and about $1\times10^{10}$ pu of the second adenoviral vector.

5. The method of claim 2, wherein the composition comprises about $1\times10^{10}$ pu to about $1\times10^{11}$ pu of the first adenoviral vector and about $1\times10^{10}$ pu to about $1\times10^{11}$ pu of the second adenoviral vector.

6. The method of claim 5, wherein the composition comprises about $5\times10^{10}$ pu of the first adenoviral and about $5\times10^{10}$ pu of the second adenoviral vector.

7. The method of claim 1, wherein the composition comprises the first adenoviral vector and does not comprise the second adenoviral vector.

8. The method of claim 7, wherein the composition comprises about $1\times10^{10}$ pu to about $1\times10^{11}$ pu of the first adenoviral vector.

9. The method of claim 8, wherein the composition comprises about $5\times10^{10}$ pu of the first adenoviral vector.

10. The method of claim 1, wherein the composition comprises the second adenoviral vector and does not comprise the first adenoviral vector.

11. The method of claim 10, wherein the composition comprises about $1\times10^{10}$ pu to about $1\times10^{11}$ pu of the second adenoviral vector.

12. The method of claim 11, wherein the composition comprises about $5\times10^{10}$ pu of the second adenoviral vector.

13. The method of claim 1, wherein each of the first and second adenoviral vectors is replication-deficient and requires complementation of both the E1 region and the E4 region of the adenoviral genome for propagation.

14. The method of claim 13, wherein the adenoviral genome of each of the first and second adenoviral vectors lacks the entire E1 region and at least a portion of the E4 region of the adenoviral genome.

15. The method of claim 14, wherein the nucleic acid sequence encoding *P. falciparum* CSP is inserted into the deleted E1 region of the adenoviral genome of the first adenoviral vector.

16. The method of claim 15, wherein the nucleic acid sequence encoding the *P. falciparum* AMA-1 antigen is inserted into the deleted E1 region of the adenoviral genome of the second adenoviral vector.

17. The method of claim 1, wherein the nucleic acid sequence encoding *P. falciparum* CSP comprises codons expressed more frequently in mammals than in *Plasmodium*.

18. The method of claim 17, wherein the nucleic acid sequence encoding *P. falciparum* CSP comprises SEQ ID NO: 10.

19. The method of claim 1, wherein the nucleic acid sequence encoding *P. falciparum* AMA-1 antigen comprises codons expressed more frequently in mammals than in *Plasmodium*.

20. The method of claim 19, wherein the nucleic acid sequence encoding *P. falciparum* AMA-1 antigen comprises SEQ ID NO: 16.

21. The method of claim 1, wherein the mammal is a human.

22. The method of claim 1, wherein the composition is administered to the mammal once.

23. The method of claim 1, wherein the composition is administered to the mammal twice.

24. The method of claim 1, wherein the priming composition is administered to the mammal at least 10 days before administration of the composition comprising the first and/or second adenoviral vectors.

* * * * *